(12) United States Patent
Shibuya

(10) Patent No.: US 8,239,141 B2
(45) Date of Patent: Aug. 7, 2012

(54) METHOD FOR CHANGING A TARGET ARRAY, A METHOD FOR ANALYZING A STRUCTURE, AND AN APPARATUS, A STORAGE MEDIUM AND A TRANSMISSION MEDIUM THEREFOR

(75) Inventor: Tetsuo Shibuya, Shimotsuruma (JP)

(73) Assignee: International Business Machines Corporation, Armonk, NY (US)

( * ) Notice: Subject to any disclaimer, the term of this patent is extended or adjusted under 35 U.S.C. 154(b) by 1234 days.

(21) Appl. No.: 11/536,102

(22) Filed: Sep. 28, 2006

(65) Prior Publication Data
US 2008/0238732 A1   Oct. 2, 2008

Related U.S. Application Data

(62) Division of application No. 09/737,190, filed on Dec. 14, 2000, now Pat. No. 7,124,034.

(30) Foreign Application Priority Data

Dec. 24, 1999  (JP) ..................................... 11-368420

(51) Int. Cl.
*G01N 33/48* (2006.01)
(52) U.S. Cl. .......................................................... 702/20
(58) Field of Classification Search ...................... 702/20
See application file for complete search history.

(56) References Cited

U.S. PATENT DOCUMENTS 5,369,577 A    11/1994   Kadashevich et al.

OTHER PUBLICATIONS

The American Heritage College Dictionary, 4th Ed., American Heritage, p. 293, 2004.
Dictionary.com, entries for array and complementary, pp. 1 and 2, 2005.
Eisen, ScanAlyze User Manual, Stanford University, pp. 1-27, 1998-1999.
Jensen, et al., "Automatic Discovery of Regulatory Patterns in Promoter Regions Based on Whole Cell Expression Data and Functional Annotation", Bioinformatics, vol. 16, No. 4, (2000), pp. 326-333.
Shibuya, Tetsuo, "Constructing the Suffix Tree With a Large Alphabet," IBM Tokyo Research Laboratory, published on Sep. 2, 1999, pp. 25-32.
Kosaraju, et al., "Large-Scale Assembly of DNA Strings and Space-Efficient Construction of Suffix Trees," Association of Computing Machinery,k published 1995, pp. 169-177; and.
Giegerich, et al., "Efficient Implementation of Lazy Suffix Trees," Springer-Veriag, Berlin Heidelberg, published 1999, pp. 30-42.

*Primary Examiner* — Jerry Lin
(74) *Attorney, Agent, or Firm* — Scully, Scott, Murphy & Presser, P.C.; Vazken Alexanian

(57) ABSTRACT

The objective of the present invention is the efficient analyzation of the structure of an array.
By performing the prev(S) calculation for a character string S, if in the character string S a like variable is present upstream of a second variable, the second variable is changed to a numerical value that indicates the distance to the upstream like variable. But if in the character string S a like variable is not present upstream of a variable, that variable is changed to "0" to obtain a character string S1. Further, by performing the compl(S) calculation for the a character string S, if in the character string S a complementary variable is present upstream of a second variable, the second variable is changed to a numerical value that indicates the distance to the complementary variable. But if in the character string S a complementary variable is not present upstream of a variable, that variable is changed to "0" to obtain a character string S2 (102). A single suffix tree (structure suffix tree) is generated by regarding the character strings S1 and S2 as a pair of corresponding character strings (104 to 114), and the obtained structure suffix tree is employed to analyze the structure of the array that is represented by the character string S.

5 Claims, 7 Drawing Sheets

METHOD FOR CHANGING A TARGET ARRAY, A METHOD FOR ANALYZING A STRUCTURE, AND AN APPARATUS, A STORAGE MEDIUM AND A TRANSMISSION MEDIUM THEREFOR

CROSS REFERENCE TO RELATED APPLICATIONS

This application is a divisional of U.S. application Ser. No. 09/737,190, filed Dec. 14, 2000 now U.S. Pat. No. 7,124,034.

BACKGROUND OF THE INVENTION

1. Technical Field

The present invention relates to a method for changing an array, and a method, an apparatus, a storage medium and a transmission medium for analyzing a structure. In particular, the present invention relates to a method for changing an array in order to analyze its structure, a method for employing the array changing method to perform the analyzation of the structure of the array, an array structure analyzation apparatus specifically provided for the employment of the array structure analyzation method, a storage medium on which is stored a program that permits a computer to implement and apply the array structure analyzation method, and a transmission medium for transmitting the program that permits a computer to implement and apply the array structure analyzation method.

2. Prior Art

Recently, the deciphering of genetic information has been completed for a variety of organisms other than human beings, and it is now anticipated that the same process of explication can be performed for the human genome. For DNA, which is the main component of chromosomes and which is represented by an array of four bases consisting of adenine (A), thymine (T), cytosine (C) and guanine (G), and for RNA, which is transcribed from DNA and which is represented by an array of four bases, in which the T in DNA is replaced by uracil (U), the analyzation of the genetic information is performed by replacing an array of the bases of a single standard DNA or RNA base array with a character string for convenience, extracting from the obtained character string the pattern of a character string that frequently appears, and analyzing the extraction results. Conventionally, as a technique, a suffix tree (a data structure) is well known that is effective for performing a rapid search of character strings to extract a character string that appears frequently, or a character string that is common to two or more character strings. The suffix tree represents all the suffixes in a character string wherein the character "$," which does not exist in a string that is currently being processed, is added at the end of the pertinent character string. An example is the character string "mississippi$" that, as is shown in FIG. 7, is obtained by adding the character "$" at the end of "mississippi," the character string that is currently being processed.

As is shown in FIG. 7, a label that corresponds to the character string is provided for each edge of the suffix tree. The first character of each label that is provided for each outgoing edge of one node (including a root node) differs from the others, and the edges are sorted in accordance with the first characters of the labels (for example, in FIG. 7, the edges are arranged in the English alphabetic order from left to right). In the suffix tree, the array of the labels that are provided for the individual edges from the root node to a specific leaf node (a node at the distal end of an edge to which no other edge is connected) is used as a suffix that corresponds to the specific leaf node (for example, "issippi$" is the suffix that corresponds to the leaf node of the array extending from the edges with labels "ppi$," "ssi" and "i" to the root node, and "ssissippi$" is the suffix that corresponds to the leaf node of the array extending from the edges with labels "ssippi$," "si" and "s" to the root node.

An algorithm is well known whereby the data structure of a suffix tree can be constructed within the time that corresponds to O(n Log s) where n denotes the length (character count) of the original character string, and s denotes the number of types of alphabetic characters that form the original character string). In particular, when the alphabet is an integer alphabet (numerals from 1 to n), the data structure of a suffix tree can be constructed within the time that corresponds to O(n). Therefore, even when a target character string is enormously long, like a character string that represents a DNA or an RNA base array, the data structure of a suffix tree for the pertinent character string can be completed within a short period of time (more specifically, a linear time relative to the length of the original character string). Further, if the suffix tree is employed, a character string having a length (character count) m can be found in the target character string within a time that corresponds to O(m log s), so that a character string used in common or a frequently appearing character string can be listed within a short period of time (a linear time relative to the length of the original character string).

In addition, when the label provided for each edge is replaced with information that represents the locations of the first character and the last character (character preceding "$") of the label in the original character string (e.g., "mississippi$" is replaced with [1●11]), the length of the character string that represents the suffix tree can be fitted to the constant times for the length of the original character string. The suffix array is also well known as a technique by which the length of the character string that represents a suffix tree can be reduced.

As was previously described, leaf nodes of a suffix tree correspond respectively to the suffixes of an original string. When the individual suffixes are arranged beginning with the suffix that corresponds to the leaf node at one end of the suffix tree (the left end in FIG. 7), an array wherein all the suffixes of an original string are arranged in dictionary order is obtained. When the suffixes that are elements of the array are replaced with data that represent the locations of the first characters of the suffixes in the original string (e.g., "ippi$" is replaced with "8"), an array (called a suffix array) having the same length as the original character string is obtained. For example, the suffix array for "mississippi" in FIG. 7 is "8 5 2 11 1 10 9 7 4 6 3."

When the above suffix array is employed, the memory capacity required for a search for a character string can be reduced compared with when a suffix tree is employed. However, the time required for searching for the character string is O(m log n), where n denotes the length of a target character string and m denotes the length of a character string that is to be searched for.

A parameterized suffix tree is also well known as a technique (a data structure) for searching for a character string that frequently appears or a character string used in common when the character string includes a variable. For a gene sequence, such as a DNA or RNA base array, a specific element in the array may be exchanged with another specific element (for example, the A and T or the G and C of DNA complement each other and can be exchanged). Thus, in a parameterized suffix tree, when replaceable elements of an array are employed as variables, and when by replacing these variables in character strings (the character strings that include the variables) the character strings can be altered so that they are the same, the character strings are regarded as being the same.

For example, when x, y and z are defined as variables and a, b and c are defined as fixed characters, "axbycxaza" and "azbxczaya" are regarded as being the same character string (called a p-string (Parameterized String)) because by exchanging the variables x, y and z the same character array can be obtained. Encoding that is expressed as prev( ) is used to detect a p-string. This encoding is used to replace variables in a character string with a numerical value (the first variable that appears is 0) that represents the distance from the same variable that appeared immediately before. When the encoding prev( ) is performed for the two previously mentioned character strings, prev(axbycxaza)=prev(azbxczaya)= a0b0c4a0a is obtained.

The parameterized suffix tree represents the result that is obtained by performing the prev( ) encoding for all the suffixes of a character string to which the character $, which is not present in a target character string, is added (this differs from a normal suffix tree that is prepared while an array obtained by performing the prev( ) encoding, for a character string to which the character $ has been added, is regarded as a normal character string). In a parameterized suffix tree, as well as a suffix tree, leaf nodes correspond to the respective suffixes. Each edge has a label that corresponds to a partial character string, and the arrangement of labels that are provided for edges from the root node to a specific leaf node represents the result obtained by the prev( ) encoding for a suffix that corresponds to the specific leaf node.

Further, in the same manner as for the suffix tree, the first character of each label, which is provided for each edge extending from a node (including the root node), differs the others, and the labels are sorted in accordance with the first character. In addition, since the labels of each of the individual edges are represented by the first and the last positions of the original character string, the data structure has the size of the constant times of length of the character string.

For a gene sequence, such as a DNA or RNA base array, it is well known that although arrays that have the same structure may have different appearances they tend to have the same functions or properties. For a DNA base array, for example, when either or both of the complementary A and T, and the complementary G and C components are exchanged with each other, or when the non-complementary A and C components are exchanged and the non-complementary T and G components are exchanged, the structure of the array (the relationship of the elements of the array) tends to be unchanged, even though the array differs from the original array, and the functions and the properties obtained by effecting the exchange tend to be similar to those of the original array. Therefore, when analyzing a gene sequence, it is extremely important that arrays having the same structure be defined as the same array, regardless of whether the array themselves are identical, and that a frequently appearing array be extracted or that a partial array commonly included in two arrays be searched for.

On the other hand, with the conventional technique for employing a suffix tree or a suffix array, a character string other than an identical one can not be defined as being the same character string, so that even though an array may have the same structure, if it has a different element arrangement it can not be treated as the same array. Further, in a parameterized suffix tree, a character string wherein variables are simply replaced is defined as being the same character string. Thus, when, for example, only A and C are exchanged in the DNA base array, or only T and G are exchanged, or when A is exchanged with C and T with A, an array having a different structure from the original array can not be distinguished from an array having the same structure as the original array. Therefore, even when any of the above conventional techniques is employed, it is difficult to efficiently analyze a gene sequence.

To resolve the above shortcomings, it is one object of the present invention to provide a method for changing an array in order to efficiently analyze the structure of the array.

It is another object of the present invention to provide a method, an apparatus, a storage medium and a transmission medium for efficiently analyzing the structure of an array.

SUMMARY OF THE INVENTION

To achieve the above objects, according to the present invention, a method for changing an array comprises the steps of: changing a variable in a target array to information that represents the location of a different variable when the target array, consisting of a combination of a plurality of various kinds of elements (all of the elements may be variables that can be replaced by other elements, or elements other than the variables may be included) is viewed along a path extending in a predetermined direction (e.g., a path extending from either end of the target array to the other end), and when a different, complementary variable is present upstream of a variable included in the target array; changing the variable to information indicating that no different, complementary variable is present when no different, complementary variable is present upstream of the variable in the target array; and repeating the steps for all the other variables included in the target array.

Through the change, the complementary variables in the array are altered to provide information that represents the positional relationships of the variables (information indicating the presence/absence of the variables as well as their locations). Thus, from an array that has a plurality of complementary variable pairs, the array changing method of the present invention produces an equivalent array (i.e., the structure of the array (the relationships of the elements of the array) is the same, even though the array itself is different) by exchanging certain of the variables in the different complementary variable pairs.

As an example, when the variable x and the variable z are complementary, and the variable y and the variable w are complementary, the array changing method of the invention (hereinafter referred to as compl( )) is used to change the array (ABxByAzwz) as follows:

compl(ABxByAzwz)=AB0B0A436.

The "0"s in the obtained array indicate that complementary variables are not present upstream, and the "4," the "3" and the "6" are used to represent distances to those complementary variables that are present upstream.

The array changing method of the present invention is employed to (1) change an array (ABzByAxwx) wherein only the complementary variables x and z are exchanged, (2) change an array (ABxBwAzyz) wherein only the complementary variables y and w are exchanged, and (3) change an array (ABwBzAyxy) wherein the variables x and w that are not complementary and the variables y and z that are not complementary are exchanged, so that all of the arrays have the same structure as the original array. The obtained arrays are:

(1) compl(ABzByAxwx)=AB0B0A436
(2) compl(ABxBwAzyz)=AB0B0A436
(3) compl(ABwBzAyxy)=AB0B0A436
and are equivalent to the original array.

The array changing method of the present invention is employed to change an array (ABwByAzxz) wherein only the variables x and w that are not complementary are exchanged, which provides an array that has a structure different from that of the original array. The obtained array is
compl(ABwByAzxz)=AB0B2A011
and thus is different from the original array.

As is apparent from above, when one pair of arrays are changed using the array changing method of the invention, the resultant arrays can be compared to efficiently determine whether the structures of the array pairs are identical, or to determine whether a sequence having the same structure is included in both the arrays. When a specific array is changed using the method of the invention, the resultant array can also be employed to easily extract a sequence having the same structure that appears frequently in the array. Therefore, according to the array changing method of the invention, the structure of an array can be changed so that an efficient analyzation of the structure of the array can be performed.

According to the array changing method of the invention, arrays having the same structure can be changed to equivalent arrays; however, although very rare, there are exceptional cases in which arrays having different structures are changed into equivalent arrays. For example, in the DNA base array, the array (TTAA) and the array (AGCC), which differ in structure, are changed by the array changing method of the invention. The resultant arrays are
compl(TTAA)=compl(AGCC)=(0012),
which are equivalent.

According to the present invention, a method for analyzing the structure of an array comprises the steps of: changing a variable that is included in a target array consisting of a combination of a plurality of different kinds of elements and that is replaceable with another element into information representing the location of the same variable when the target array is viewed along a path extending in a predetermined direction, and when the same variable is present upstream of the variable; and changing, when the same variable is not present upstream of the replaceable variable in the target array, all the variables in the target array into information indicating that the same variable is not present, and thus changing the target array into a first array.

By changing the target array to a first array, the variables in the target array are converted to data (data that represent the presence/absence of the same variable and its location) that represents the positional relationship of the same variable in the array. Thus, one pair of arrays that have different structures but are changed to equivalent arrays by the method of the invention can be changed as first arrays that differ from each other. For example, the arrays (TTAA) and (AGCC), which are to be changed to equivalent arrays by the array changing method of the invention, are changed to the following first arrays that differ from each other:
prev(TTAA)=(0101) prev(AGCC)=(0001)
The "0"s in the obtained first array indicate that the same variables are not present upstream, and the "1"s represent distances to the same variables that are present upstream.

According to the method for analyzing the structure of an array, in the above manner, the target array is changed to the first array and is also changed to a second array by the array changing method of the present invention, and the first and the second arrays are employed to analyze the structure of the target array. Thus, the array for which the first and the second arrays obtained by the process are equivalent is determined to be the same array, so that the array having a different structure can be excluded and only the array having the same structure can be precisely identified. As a result, the structure of the array can be efficiently analyzed.

Various analyzation methods are available for employing the first and the second arrays to analyze the structure of the array. As an example method, a suffix tree is prepared by using the first and the second arrays and is employed to analyze the structure of the array. This method is preferable because the process can be completed within a shorter time than can the other analyzation methods. To prepare the suffix tree, for example, in an operation to prepare a single suffix tree the first and the second arrays are regarded as a single pair of corresponding character strings. Then, from among sequences of the first and the second arrays, which are provided as labels for individual edges of the single suffix tree, information that indicates the location of the same variable or the different variable that is not present in each of the sequences is replaced with information that indicates the absence of the same variable or the different variable.

The target array is changed to the first and the second arrays by using, as information that indicates the position of the same variable in the first array and the position of a different variable in the second array, numerical information that represents the number of elements arranged in the target array beginning at the position of a target variable and continuing up to the position of same variable, or a different variable. In this process, if it is ascertained that, when one pair of arrays are changed to the first and the second arrays, one (array A) of the first and the second arrays matches, and that in the other array (array B), numerical information that is located at a position corresponding to the information indicating that, at the least, the different variable or the same variable in the array A is not present, it is ascertained that the array B obtained from the array pair also matches and that the pair of arrays have the same structure.

For the first and the second thus obtained arrays, all of the information indicating that the different variable or the same variable is not present in the target array is replaced with numerical information, obtained by inverting the positive and negative signs of the numerical information, indicating the number of elements that are present in another array at locations corresponding to the information. Then, by regarding the obtained array as a character string, a suffix tree is prepared as follows. Among the sequences of the obtained array that are provided as labels for edges of the suffix tree, numerical information indicating the positioning of the same variable or the different variable that is not present in each of the sequences is replaced with information indicating that the same variable or the different variable is not present.

When the suffix tree prepared in the above described manner is employed, it is extremely easy to extract a sequence that has the same structure and that frequently appears in the target array, which is one type of process used for the analyzation of the structure of the target array.

Further, when searching for a common sequence in a first target array and a second target array, which is one type of process used for the analyzation of the structure of a target array, a suffix tree is prepared by using, as the target array (an array for which suffixes are to be prepared), an array wherein the first target array, first identification information, the second target array and second identification information are arranged in order. Then, when the thus prepared suffix tree is employed, it is extremely easy to search for the common sequence.

The suffix tree employs a tree structure to represent all the suffixes that are present in a character string when the character string is viewed along a path extending in a specific direction. The suffix in the character string is a prefix as viewed from the opposite direction. While taking into account the analyzation of the structure of the array, a prefix tree that employs a tree structure to represent all the prefixes in the character string is also logically equivalent to the suffix tree. Therefore, instead of the suffix tree, the prefix tree may be employed for this invention.

According to the present invention, an apparatus for analyzing the structure of an array comprises: first conversion means for changing a target array into a first array by converting, in the target array, a variable that is replaceable by another element into information indicating the position of the same variable or information indicating the absence of the same variable; second conversion means for changing the target array into a second array by converting, in the target array, a variable that is replaceable by another element into information indicating the position of a different, complementary variable, or information indicating the absence of the different, complementary variable; and analyzation means for employing the first and the second arrays to analyze the structure of the target array. With this apparatus, as well as by applying the method of the invention for analyzing the structure of the array, the structure of the array can be efficiently analyzed.

According to the present invention, a storage medium is provided on which is stored a program that permits a computer to implement the method of the invention to analyze the structure of an array, i.e., that permits a computer to perform the processing comprising: a first step of changing a target array into a first array by converting, in the target array, a variable that is replaceable by another element into information indicating the position of the same variable or information indicating the absence of the same variable; a second step of changing the target array into a second array by converting, in the target array, a variable that is replaceable by another element into information indicating the position of a different, complementary variable, or information indicating the absence of the different, complementary variable; and a third step of employing the first and the second arrays to analyze the structure of the target array. With this apparatus, as well as by applying the method of the invention for analyzing the structure of the array, the structure of the array can be efficiently analyzed. Since the computer reads the program from the storage medium and executes it, the structure of the array can be efficiently analyzed in the same manner as in the method of the invention used for analyzing the structure of the array.

According to the present invention, a transmission medium is provided for transmitting a program that permits a computer to perform the method of the invention by analyzing the structure of an array, i.e., a program that permits a computer to perform the processing comprising: a first step of changing a target array into a first array by converting, in the target array, a variable that is replaceable by another element into information indicating the position of the same variable or information indicating the absence of the same variable; a second step of changing the target array into a second array by converting, in the target array, a variable that is replaceable by another element into information indicating the position of a different, complementary variable, or information indicating the absence of the different, complementary variable; and a third step of employing the first and the second arrays to analyze the structure of the target array. With this apparatus, as well as by applying the method of the invention for analyzing the structure of the array, the structure of the array can be efficiently analyzed. Therefore, when the computer uses storage means to temporarily store the program received from the transmission medium, and then reads the program from the storage means and executes it, the structure of the array can be efficiently analyzed in the same manner as it is when the method of the invention is used that is specifically provided for the analyzation of the array structure.

BRIEF DESCRIPTION OF THE DRAWINGS

Preferred embodiments of the present invention will now be described, by way of example only, with reference to the accompanying drawings in which.

DETAILED DESCRIPTION OF THE PREFERRED EMBODIMENTS OF THE INVENTION

Figure 1:
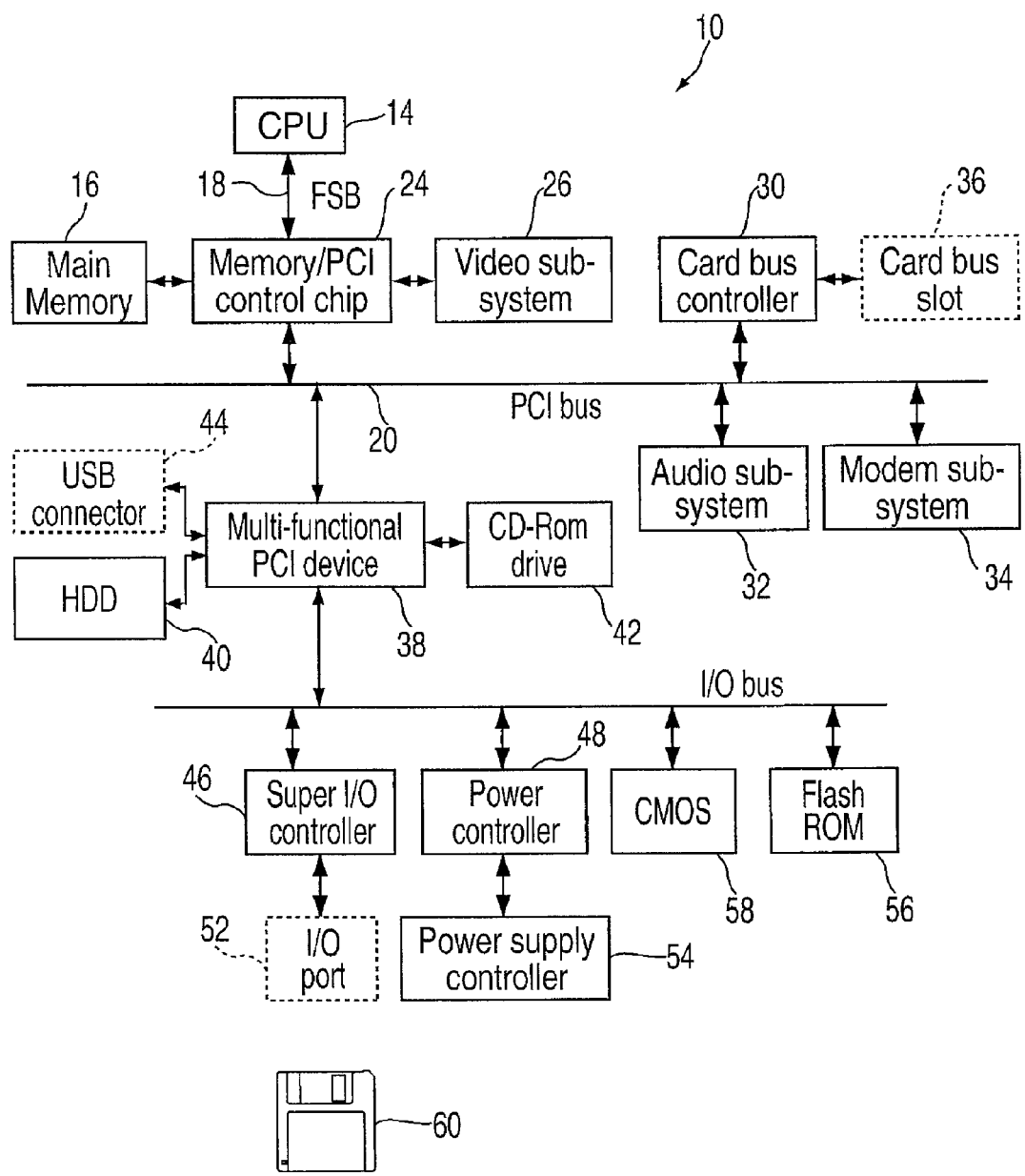
FIG. 1 is a schematic block diagram illustrating the arrangement of a computer system according to one embodiment of the present invention.

The preferred embodiment of the present invention will now be described in detail while referring to the drawings.

FIG. 1 is a specific diagram illustrating, for each subsystem, the hardware arrangement of a computer system 10 comprising a personal computer (PC) that is appropriate for the present invention. An example PC for carrying out the present invention is either a notebook or a desktop PC that conforms to the OADG (PC Open Architecture Developer's Group) specifications, and on which is mounted, as an operating system (OS), "Windows98" or "NT," by Microsoft Corp., or "OS/2," by IBM. The individual sections of the computer system 10 will now be described.

A CPU 14, which is the brain of the entire computer system 10, executes various programs under the control of the OS. The CPU 14 may, for example, be a "Pentium," "MMX technology Pentium" or "Pentium Pro" by Intel Corp., a "Power PC" by IBM, or a CPU by another maker, such as AMD Corp. The CPU 14 includes an L2 (level 2)-cache, which is fast operating memory, for temporarily storing very limited code or data that are frequently accessed so as to reduce the total time required to access a main memory 16. The L2-cache is generally constituted by an SRAM (Static RAM) chip that has a memory capacity of at least 512 kB.

The CPU 14 is connected to the individual hardware components, which will be described later, via three bus layers, including: an FSB 18, which is a processor bus directly connected to the external pin of the CPU 14; a PCI (Peripheral Component Interconnect) bus 20, which is a fast I/O bus; and an I/O bus 22, which is an ISA (Industry Standard Architecture) bus for low speed I/O.

The FSB 18 and the PCI bus 20 are generally connected by a bridge circuit (host-PCI bridge) that is called a memory/PCI control chip 24. In this embodiment, the memory/PCI control chip 24 includes a memory controller function for controlling the access to the main memory 16 and a data buffer for absorbing the difference in data transmission speeds between the FSB 18 and the PCI bus 20. A 440EX or a 440GX by Intel Corp. can be employed as the memory/PCI control ship 24.

The main memory 16 is a writable area that is used as a reading area for a program for the CPU 14, or as a work area for writing data processed by the program. The main memory 16 is generally constituted by a plurality of DRAM (Dynamic RAM) chips. As a standard, 32 MB of memory is mounted, but this can be expanded to 256 MB. Recently, in order to respond to requests for high-speed processing, DRAM has been exchanged for fast page DRAM, EDO DRAM, synchronous DRAM (SDRAM), burst EDO DRAM, or RDRAM.

The programs herein include firmware, such as the OS, represented by Windows98, various device drivers for operating peripheral devices, application programs for specific jobs, and a BIOS (a Basic Input/Output System: a program for controlling the input/output operation of hardware components, such as keyboards and floppy disk drives) that is stored in a flash ROM 56 (which will be described in detail later).

The PCI bus 20 is a bus for comparatively rapid data transmission (e.g., a bus width of 32/64 bits, with a maximum operating frequency of 33/66/100 MHz and a maximum data transmission speed of 132/264 MBps). The PCI bus 20 is connected to a PCI device, such as a card bus controller 30, that is driven at a comparatively high speed. It should be noted that the PCI architecture originally was advocated by Intel Corp., and that a so-called PnP (Plug and Play) function is provided and employed.

A video sub-system 26, which includes a video controller, performs a video associated function. Actually, the video controller handles drawing commands received from the CPU 14, temporarily writes obtained drawing data in a video memory (VRAM), and reads the drawing data from the VRAM and outputs it to a liquid crystal display (LCD). The video controller also employs an attached digital-analog converter (DAC) to convert digital video signals to analog video signals. The analog video signals are output via a signal line to a CRT port (not shown).

The PCI bus 20 is also connected to the card bus controller 30, an audio sub-system 32 and a modem sub-system 34. The card bus controller 30 is a special controller for directly transmitting a bus signal carried by the PCI bus 20 to the interface connector (card bus) of a PCI card bus slot 36. The card bus slot 36 is formed, for example, in the wall of the main body of the PC, and a PC card (not shown) that conforms to the standards (e.g., "PC Card Standard 95") determined by the PCMCIA (Personal Computer Memory Association)/JEIDA (Japan Electronic Industry Development Association) is loaded into the card bus slot 36.

Connected to the modem sub-system 34 is a communication line, such as a LAN line or a telephone line, that can be used to connect the computer system 10 to the Internet.

The PCI bus 20 and the I/O bus 22 are interconnected by a multi-functional PCI device 38. The multi-functional PCI device 38 includes a function for bridging the PCI bus 20 and the I/O bus 22, a DMA controller function, a programmable interrupt controller (PIC) function, a programmable interval timer (PIT) function, an IDE (Integrated Drive Electronics) interface function, a USB (Universal Serial Bus) function and an SMB (System Management bus) interface function. A PIIX4, for example, by Intel Corp. can be used as the multi-functional PCI device 38.

The DMA controller function transmits data between a peripheral device (e.g., an FDD) and the main memory 16, without the CPU 14 being required. The PIC function executes a predetermined program (an interrupt handler) in response to an interrupt request (IRQ) received from a peripheral device. And the PIT function, which has a programmable generation cycle, generates a timer signal each predetermined cycle.

An IDE interface, which is implemented by the IDE interface function, is used to connect to an IDE hard disk drive (HDD) 40, and ATAPI (AT Attachment Packet Interface) is used to connect an IDE CD-ROM drive 42, or may instead be used to connect another type of IDE device, such as a DVD (a Digital Video Disc or a Digital Versatile Disc) drive. External devices, such as the HDD 40 and the CD-ROM drive 42, are stored in locations called "media bays" or "device bays." The external storage devices that are mounted as standard may be so provided that they can or can not be replaced by other devices, such as FDDs or battery packs.

The main memory 16 corresponds to a main storage device for the present invention, and the HDD 40 corresponds to a secondary storage device for the present invention.

A USB port is provided for the multi-functional PCI device 38, and is connected to a USB connector 44 that is provided, for example, on the wall of the PC main body. The USB supports a function (a hot plugging function) for the insertion and removal of peripheral devices (USB devices) while the power is on, and a function (a plug and play function) for automatically recognizing a newly connected peripheral device and for resetting the system configuration. A maximum of 63 USB devices can be daisy-chain connected to one USB port. Example USB devices are a keyboard, a mouse, a joy stick, a scanner, a printer, a modem, a display monitor and a tablet.

In addition, an EEPROM (not shown) is connected via an SM bus to the multi-functional PCI device 38. The EEPROM is a nonvolatile, electrically rewritable memory for storing information, such as a password that is registered by a user, a supervisor password and a product serial number.

The I/O bus 22 has a lower data transmission speed than the PCI bus 20 (e.g., a bus width of 16 bits and a maximum data transmission speed of 4 MBps). Connected to the I/O bus 22 are a Super I/O controller 46, a power controller 48, the flash memory 56 consisting of an EEPROM, CMOS RAM 58, and a peripheral device (not shown) such as a real time clock (RTC) or a keyboard/mouse controller that is operated at a comparatively low speed.

Connected to the Super I/O controller 46 is an I/O port 52 that serves as a peripheral controller for driving a floppy disk drive (FDD), for controlling the input/output (PIO) of parallel data via a parallel connection and the input/output (SIO) of serial data via a serial connection.

The power controller 48 is mainly used to control the power management or the thermal management of the computer system 10, and can be constituted by a single-chip micro computer that includes an MPU, a RAM, a ROM and a timer. In the ROM are stored a program and a reference table that are required to execute the power management and the thermal management functions. The power controller 48, which is connected to a power supply controller 54, includes a charger for charging a battery and a DC/DC converter for generating a constant DC voltage, such as 5 V or 3.3 V, that is used by the computer system 10. The supply of power by the controller 54 is controlled by the power controller 48.

The flash ROM 56 is composed of nonvolatile memory used to store a firmware program, such as the BIOS or boot strap code, and the contents stored therein can be electrically rewritten. The CMOS RAM 58, which is provided by connecting a semiconductor memory to a backup power source, functions as nonvolatile, fast storage means.

Many electric circuits in addition to those in FIG. 1 are required to constitute the computer system 10. However, since these are well known to one having ordinary skill in the art, and since those electric circuits are not directly related to the subject of the invention, no further explanation will be given for them in this specification. Furthermore, to avoid complexity in the drawings, only a part of the connections for the hardware blocks in FIG. 1 are shown.

The processing for the invention will now be described. A method for changing an array and a method for analyzing the structure of an array of the present invention will be implemented by a program for analyzing the structure of an array. Several methods are used to install the structure analyzation program into the computer system 10. For example, to install the structure analyzation program a setup program, along with the structure analyzation program, is stored on a data storage medium 60 (see FIG. 1), such as a floppy disk. The data storage medium 60 is inserted into an FDD that is connected to an I/O port 52 in the computer system 10, and an instruction is issued to the CPU 14 to execute the setup program. Following this, the structure analyzation program is installed by being sequentially read from the data storage medium 60 and written on the HDD 40.

When an instruction for the generation of a suffix tree is issued to a computer system 10 that has been powered on and is ready to operate, the CPU 14 reads the structure analyzation program from the HDD 40 and executes it. Thus, the computer system 10 functions as an apparatus according to the present invention for analyzing the structure of an array. As is apparent from the above description, the data storage medium 60 corresponds to a storage medium according to the present invention.

While referring to the flowchart in FIG. 2, an explanation will be given for the suffix tree generation processing performed when the CPU 14 executes a suffix tree generation program, which is one part of the structure analyzation program.

At step 100 a character string S (a target array) to be processed (to be analyzed) is fetched. The target character string S can be a character string that represents a single-stranded DNA base array by replacing the four bases (adenine, thymine, cytosine and guanine) with four characters, "A," "T," "C" and "G" respectively, or a character string that represents an RNA base array by replacing four bases (adenine, uracil, cytosine and guanine) with characters "A," "U," "C" and "G". An end identification character (a character, such as "$," that is not present in a character string) that is used to identify a character string end, is added to the character string S that is fetched at step 100.

Hereinafter, the i-th character of the character string S is denoted by S[i], a character string part that begins with the j-th character of the character string S and ends with i-th character is denoted by S[j . . . i], and the length of the character string S (the character count) is denoted by n (i.e., S[1 . . . n]=the character string S).

Figure 3:
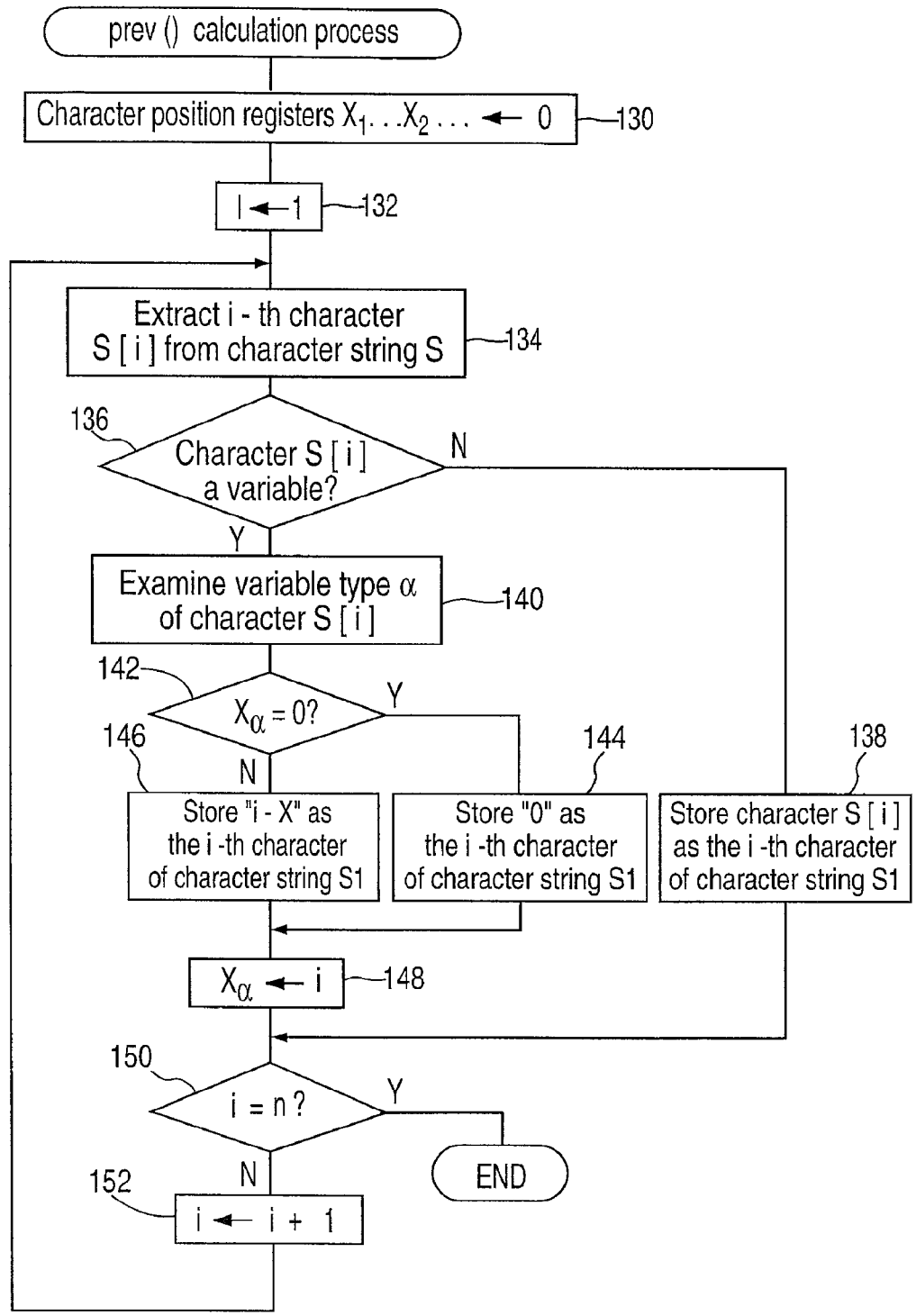
FIG. 3 is a flowchart showing the prev ( ) calculation processing.

At step 102, the character string S is changed to a first character string S1 in accordance with a changing condition prev( ) (prev(S)=S1), and is also changed to a second character string S2 in accordance with a changing condition compl( ). The conversion of the character string S into the first character string S1 can be performed by the prev( ) calculation process in FIG. 3, for example. The prev( ) calculation process corresponds to the conversion to the first array for which the structure analyzation method is used. This process will now be described.

At step 130, "0"s are set for character position registers $X_1$, $X_2$, . . . . The character position registers are provided in a number equivalent to the types of variables that are included in the character string S (variables here are characters that are replaceable with other characters (variables) during the analyzation of the structure of the character string S: e.g., "A," "T," "C" and "G" for the character string that represents the single-stranded DNA base array, and "A," "U," "C" and "G" for the character string that represents the RNA base array.) At step 132, "1" is substituted into a counter i.

At step 134, the i-th character S[i] is extracted from the character string S, and at step 136, a check is performed to determine whether the character S[i] is a variable. When it is determined that the character S[i] is not a variable (for example, when the character string S represents the DNA or RNA base array and the character S[i] is an end identification character, or when the character string S also includes characters other than variables and the character S[i] represents an entry other than a variable), program control is shifted to step 138. The character S[i] is stored as the i-th character of the first character string S, and program control is shifted to step 150.

When the character S[i] is a variable, the decision at step 136 is affirmative, and program control advances to step 140, whereat a variable type a of the character (variable) S[i] is examined. At step 142, a check is performed to determine whether a numerical value of "0" has been set for a character position register $X\alpha$ that corresponds to the variable type $\alpha$ of the character (variable) S[i]. When a numerical value of "0" has been set for the character position register $X\alpha$, it is assumed that the character S[i] is a variable of a variable type $\alpha$ that appears first, and that the same variable (a variable of the same variable type $\alpha$) is not present upstream of the character S[i] in the character string S.

When the decision at step 142 is affirmative, program control is shifted to step 144. A value of "0" (information indicating that the same variable is not present upstream of the character S[i] in the character string S) is stored as the i-th character of the first character string S1. Program control is then shifted to step 148. At step 148, the value of the counter i (information that represents the position of the character S[i] of the character string S) is substituted into the character position register $X\alpha$. Therefore, when a variable of the variable type $\alpha$ appears next, an affirmative decision is obtained at step 142.

At step 152, a check is performed to determine whether the value of the counter i matches the length (the character count) n of the character string S. When the decision at step 152 is negative, the value of the counter i is incremented by one. Program control then returns to step 134, the next character is extracted as the character S[i], and the processing following step 136 is repeated.

When the character S[i] is a variable and a like variable appeared previously, the decision at step 136 is affirmative, the decision at step 142 is negative, and program control advances to step 146. At step 146, "i-$X\alpha$" is stored as the i-th character of the first character string S1, and program control advances to step 148. At this time, since the position in the character string S of the variable that appeared previously, which is the same as that represented by the character S[i], is stored in the character position register $X\alpha$, "i-$X\alpha$" constitutes numerical information that indicates the upstream position, relative to the character S[i], in the character string S of the previously stored variable (more specifically, information that indicates the distance from the character S[i] to a like variable that appeared previously).

Through the prev( ) calculation process, when upstream in a character string S a like variable or like variables are present, a variable downstream of a like variable that appeared previously is converted into a numerical value representing the distance to the variable that appeared previously. When there is no like upstream variable, a variable in the character string S is changed to "0." Thus, for example, the character string S(AUAUCGU$), which represents an RNA base array, is changed to the following first character string S1.
prev(AUAUCGU$)=S1=(0022003$)

Figure 4:
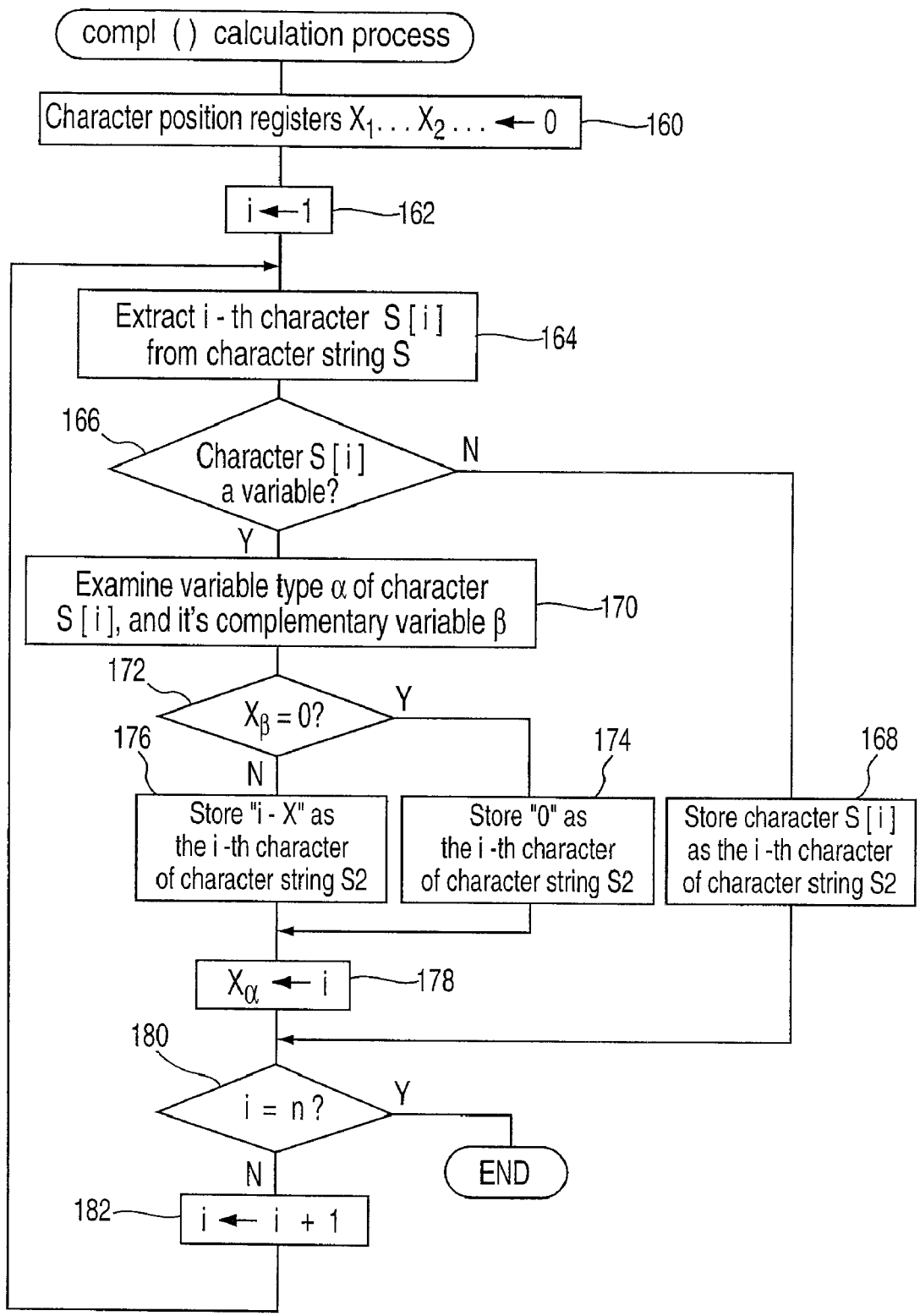
FIG. 4 is a flowchart showing the compl ( ) calculation processing.

In addition, the conversion of the target string S into a second character string S2 can be performed using the compl( ) calculation process in FIG. 4. The compl( ) calculation process corresponds to the conversion to the second array by the array changing method and the structure analyzation method of the present invention. The compl( ) calculation process will now be described.

In the compl( ) calculation process, a pair of complementary variables are determined in advance for a variable included in the character string S. For example, for a character string S that represents the single-stranded DNA base array, two pairs of complementary variables, A and T, and C and G, are determined in advance, based on the actual relationship existing between the individual bases in the DNA base array. For a character string S that represents the RNA base array, two pairs of complementary variables, A and U, and C and G are determined in advance based on the actual relationship of the individual bases in the RNA base array.

At step 160, a value "0" is set for the character position registers $X_1, X_2, \ldots$, and at step 162 a value "1" is substituted into the counter i. At step 164, the i-th character S[i] is extracted from the character S, and at step 166 a check is performed to determine whether the character S[i] is a variable or not. When the decision at step 166 is negative, program control is shifted to step 168, whereat the character S[i] is stored as the i-th character of the second character string S2. Program control is then shifted to step 180.

When the character S[i] is a variable, the decision at step 166 is affirmative, and program control advances to step 170. The variable type α of the character (variable) S[i] is examined, and the variable type β, which is the complementary variable of the variable type α, is examined (in this case, if the character S[i] is "A," "T," "C" or "G," respectively, the type β of "T," "A," "G" or "C" is examined). At step 172, a check is performed to determine whether a numerical value of "0" has been set for the character position register Xβ for the variable type β that is the complementary of the character (variable) S[i]. If the character position register Xβ has been set for the numerical value of "0," it is assumed that a variable of the variable type β has not yet appeared, and that a different variable (a variable of variable type β), the complementary variable of the character S[i] of the character string S, is not present upstream of the character S[i].

Therefore, when the decision at step 172 is affirmative, program control is shifted to step 174. A value of "0" (information indicating that a different, complementary variable is not present upstream of the character S[i] in the character string S) is stored as the i-th character of the second character string S2. Program control is thus shifted to step 178. At step 178, the value of the counter i (information indicating the position of the character S[i] of the character S) is substituted into the character position register Xα. Thus, when a variable of a complementary variable type β appears next, the affirmative decision is obtained at step 172.

At step 182, a check is performed to determine whether the value of the counter i matches the length (character count) n of the character string S. When the decision is negative, at step 182, the value of the counter i is incremented by one, and program control returns to step 164, whereat the character S[i] is extracted. Thereafter, the processing following step 166 is repeated.

When the character S[i] is a variable and when a different complementary variable of the character S[i] appeared previously, the decision at step 166 is affirmative, the decision at step 172 is negative, and program control advances to step 176. At step 176, "i-Xβ" is stored as the i-th character of the second character string S2, and program control advances to step 178. At this time, since the position in the character string S of the different complementary variable of the character (variable) S[i] that appeared previously is stored in the character position register Xβ, "i-Xβ" is numerical information indicating the position in the character string S of the different complementary variable of the character S[i] that is present upstream of the character S[i] (more specifically, numerical information that represents the distance from the character S[i] to the complementary variable that appeared previously).

Through the above described compl( ) calculation processing, when a complementary variable or variables are present upstream of variables in the character string S, all the variables in the character string S are changed to numerical values, each of which represents the distance to a complementary variable. However, when a complementary variable is not present upstream of a variable, the specific variable is changed to "0." Thus, for example, the character string S(AUAUCGU$), which represents the RNA base array, is changed to the following second character string S2.
compl(AUAUCGU$)=S2=(0111014$)

Figure 2:
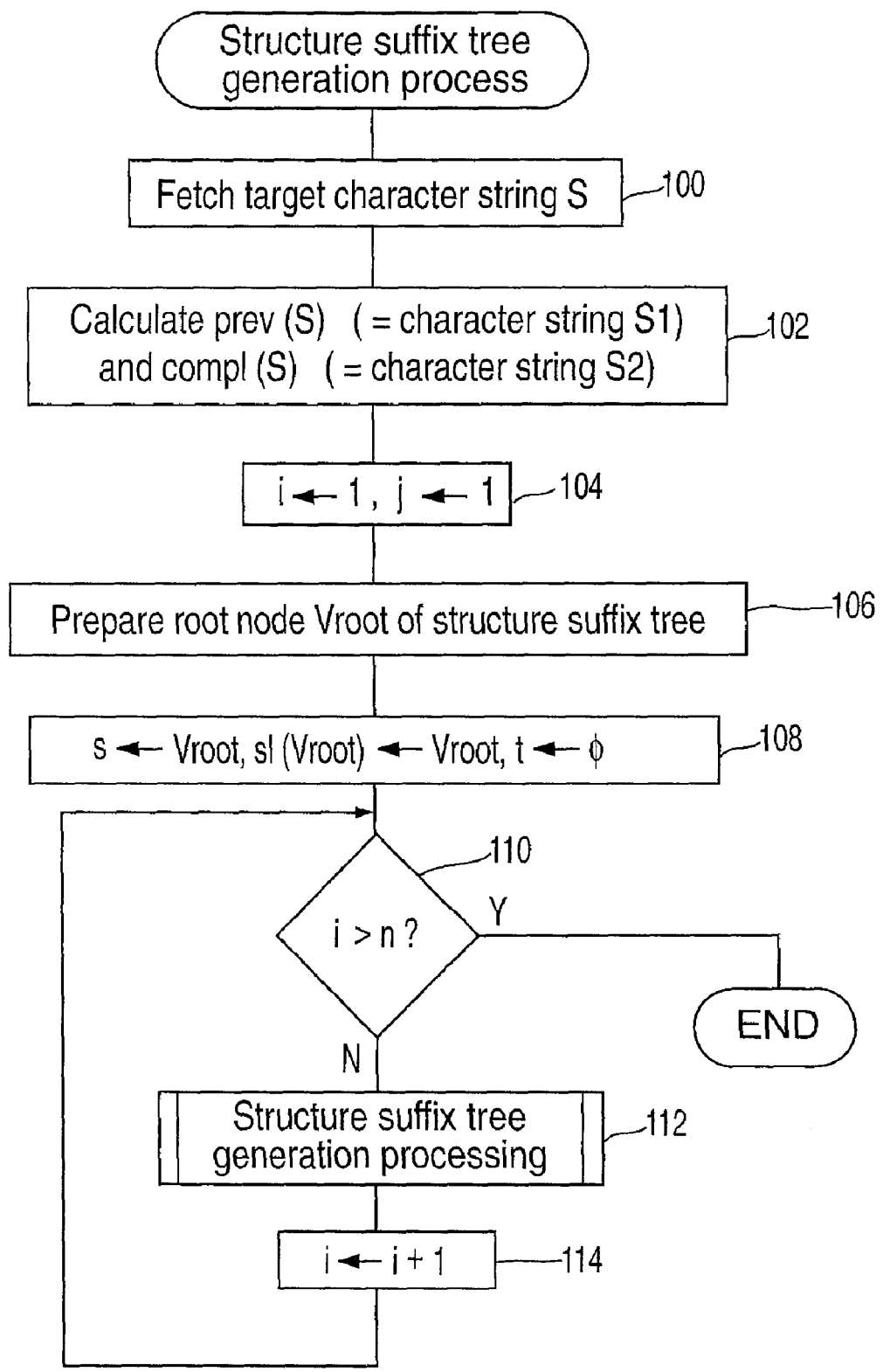
FIG. 2 is a flowchart showing the structure suffix tree generation processing according to the embodiment of the present invention.

When the target character string S has been changed to the first character string S1 and the second character string S2, program control is shifted to step 104 in the flowchart in FIG. 2. At step 104 and the following steps, the first character string S1 and the second character string S2 are regarded as a pair of corresponding character strings, and are employed to generate a single suffix tree (referred to as a structure suffix tree). A label that corresponds to a portion of a character string in the first character string S1 and a label that corresponds to the second character string S2 are provided for the individual edges of the structure suffix tree that is generated below.

Further, in the following explanation, label(V) denotes a label string (character string) that is obtained by coupling labels that are provided for all the edges along the path extending from a node V to a root node Vroot. V( . . . ) denotes a node having " . . . " as a label (label(V)=" . . . "). V(φ) denotes the root node Vroot, and E( . . . ) denotes an edge between the node V, whereat the character string " . . . " is the suffix for label (V), and the parent node of the node V. f( . . . ) denotes a function for replacing the k-th (k is an arbitrary integer) character (numerical value) of character string ( . . . ) with "0" when the k-th character is a value equal to or greater than k.

First, at step 104, "1"s are substituted into the counters i and j, and at step 106, the root node Vroot of the structure suffix tree is prepared. At step 108, the root node Vroot is substituted into a parameter s, which is used to point to a node that corresponds to a search start position whereat, for a search, tracing of the structure suffix tree is initiated. And φ (empty set) is substituted into a temporary t, for temporarily storing the information, and the root node Vroot is substituted into an area sL(Vroot), which is used to point to a specific node.

In the structure suffix tree, the area sL( ) is an area that is provided while corresponding to each of the nodes except for the leaf nodes. In the area sL(V) of the node V, either information indicating a node W, for which label(W) is a character string obtained by removing the first character from label(V) (i.e., sL(V)=W), or information indicating a parent node of an edge, wherein the node W seems to be present, is set, which will be described later. Since label(Vroot)=φ, sL(Vroot) b Vroot is defined for the convenience sake.

At step 110, a check is performed to determine whether the value of the counter i is greater than the character count n of the target character string S. When the decision is negative, at step 112 the structure suffix tree generation process is performed, which will be described later. After the structure suffix tree generation process has been performed, at step 114 the value of the counter i is incremented by one, and program control returns to step 110. Therefore, during a period continuing until i>n is established, the structure suffix tree generation process is repeated while the value of the counter i is incremented. The structure suffix tree generation process at step 112 will now be described while referring to the flowchart in FIG. 5. To make the process easier to understand, (AUAUCGUAUA$) is employed as the target character string S (i.e., the first character string S1=(0022003$) and the second character string S2=(0111014$)). However, in the structure suffix tree generation process, the structure suffix tree for an arbitrary character string can be generated.

At step 200, the structure suffix tree is traced beginning at a node s (the root node Vroot at first) and moving toward a leaf node to search for an edge of E(f(S1 [j ... i−1])) and E(f(S2[j ... i−1])). Since S1[j ... i−1] and S2[j ... i−1], for example, are both φ when i=j=1, f(S1[j ... i−1]) and f(S2[j ... i−1]) are also φ. At this time, since a node other than the root node Vroot and an edge are not present along the structure suffix tree, the edge of E(f(S1 [j ... i−1])) and E(f(S2[j ... i−1])) is not found.

At step 202, a check is performed to determine whether an edge of E(f(S1[j ... i])) and E(f(S2[j ... i])) is present. When, for example, i=j=1, and S1=(0022003$) and S2=(0111014$), S1[j ... i]=S1[1]=(0) and S2[j ... i]=S2[1]=(0), so that f(S1[j ... i])=(0) and f(S2[j ... i])=(0) are obtained. At this time, since a node other than the root node Vroot and an edge are not present along the structure suffix tree, the decision at step 202 is negative. And when the decision at step 202 is negative, program control advances to step 204 and a check is performed to determine whether a node of V(f(S1[j ... i−1])) and V(F(S2[j ... i−1])) is present. If i=j=1, f(S1[j ... i−1]) and f(S2[j ... i−1]) are both φ, as was previously remarked. However, since V(φ) represents Vroot, the decision at step 204 is affirmative, and program control is shifted to step 206. At step 206, "NO" is substituted into flag node#constructed, and program control is thereafter shifted to step 212.

At step 212, a check is performed to determine whether the temporary t is φ. Since the temporary t is initially set to φ at step 108 (FIG. 2), the decision at step 212 is affirmative, and program control is shifted to step 218, whereat a check is performed to determine whether the flag node#constructed indicates "YES." Since at step 206 "NO" was substituted into the flag node#constructed, the decision at step 218 is negative, and program control is shifted to step 220. A node that is designated by the area sL( ) of the node (the root node Vroot in this case) of V(f(S1[j ... i−1])) and V(f(S2[j ... i−1])) is substituted into the parameter s. Since at step 108 Vroot was substituted into the sL(Vroot), the root node Vroot is substituted into the parameter s. When the process at step 200 is performed next, the search is initiated beginning at the node that is stored in the parameter s.

Figure 6:
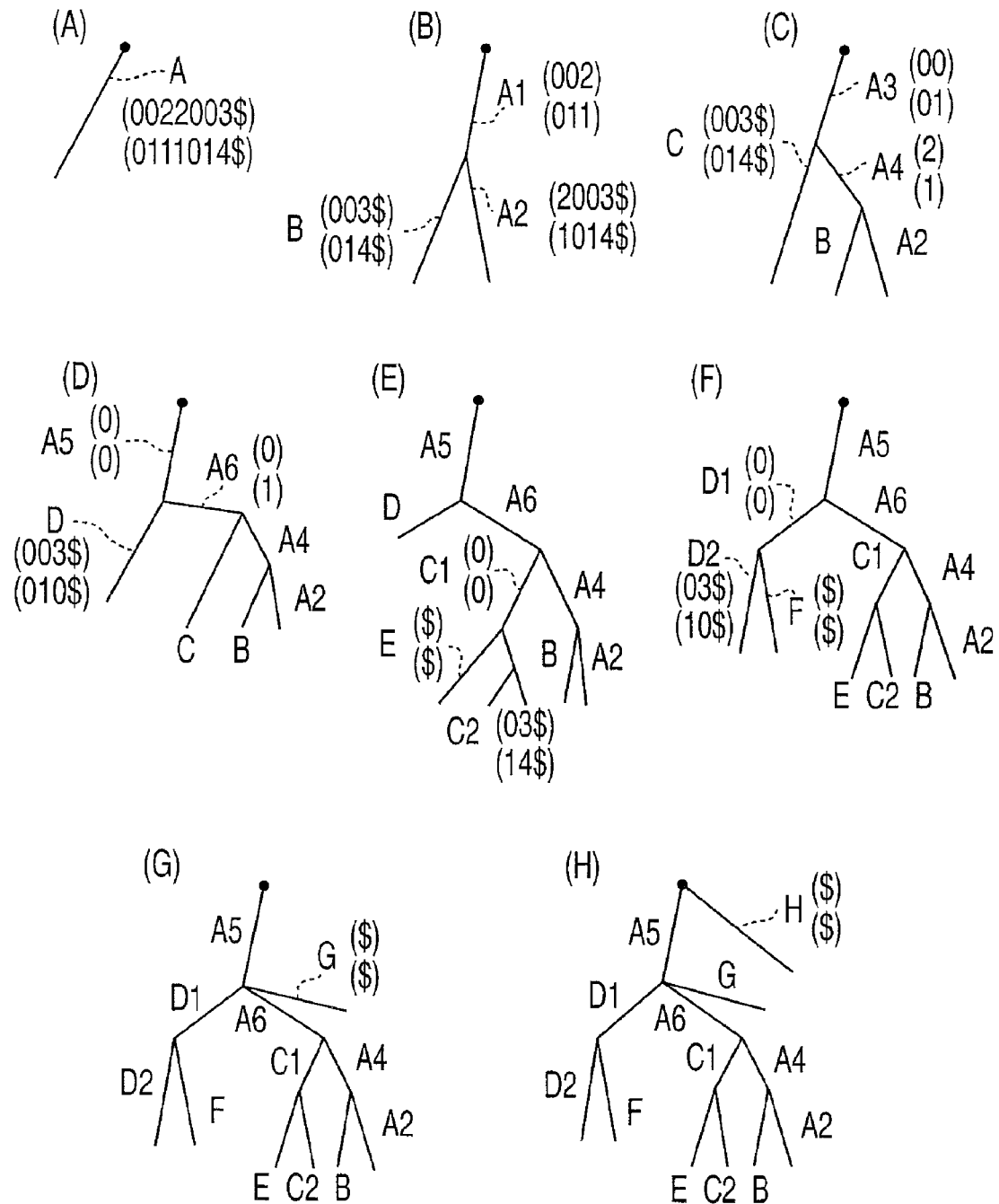
FIGS. 6A to 6H are conceptual diagrams showing example processing for preparing a structure suffix tree according to the embodiment.
Figure 7:
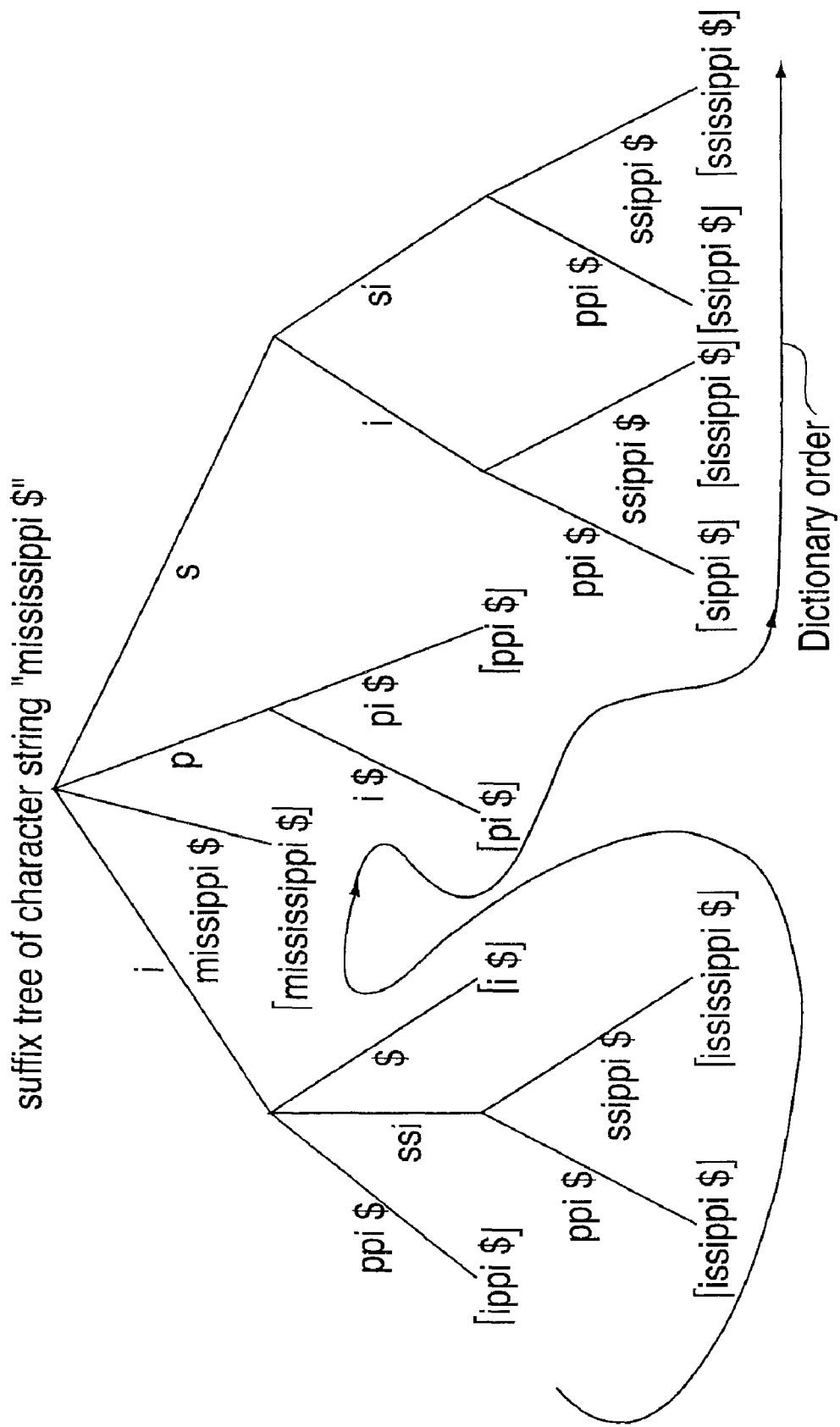
FIG. 7 is a conceptual diagram showing an example suffix tree.

Program control is then shifted from step 220 to step 226. At step 226, a child node is prepared for the node (the root node Vroot in this case) of V(f(S1[j ... i−1])) and V(f(S2[j ... i−1])), and labels obtained by removing f(S1[j ... i−1]) from f(S1[j ... ]) and by removing f(S2[j ... i−1]) from f(S2[j ... ]) are provided for an edge from the prepared child node. Therefore, as is shown in FIG. 6A, the child node (leaf node) is generated for the root node, and labels that are obtained by removing f(S1[j ... i−1]) from f(S1[j ... ]) (since f(S1[j ... i−1])=φ, label (0022003$)) and by removing f(S2[j ... i−1]) from f(S2[j ... ]) (since f(S2[j ... i−1])=φ, label (0111014$)) are provided for an edge (edge labeled A).

At step 228, the value of the counter j is incremented by one, and at step 230, the value of the counter j is greater than the value of the counter i. Since i (=1)<j (=2), the decision at step 230 is affirmative, and the structure suffix tree generation process is temporarily halted. When the counter i is incremented by one (step 114 in FIG. 2), the structure suffix tree generation process is resumed under the condition wherein i=j=2.

Since S1[j ... i−1] and S2[j ... i−1] are both φ when i=j=2, f(S1[j ... i−1]) and f(S2[j ... i−1]) are both φ and the edge of E(f(S1[j ... i−1])) and E(f(S2[j ... i−1])) are φ. Since f(S1[j ... i])=f(S1 [2])=(0) and f(S2[j ... i])=f(S2[2])=(0), the edge of E(f(S1[j ... i])) and E(f(S2[j ... i])) is present (edge A). Therefore, the decision at step 202 is affirmative, and program control is shifted to step 232. Then, the parent node (the root node Vroot in this case) of the edge of E(f(S1[j ... i])) and E(f(S2[j ... i])) is substituted into the parameter s. At step 234, a check is performed to determine whether the temporary t is φ. In this case, the decision at step 234 is affirmative, and the structure suffix tree generation process is temporarily halted. When the value of the counter i is incremented by one, the structure suffix tree generation process is resumed under the condition wherein i=3 and j=2.

Since, with i=3 and j=2, f(S1[j ... i−1])=f(S1[2])=(0) and f(S2[j ... i−1])=f(S2[2])=(0), at step 200 the edge of E(f(S1[j ... i−1])) and E(f(S2[j ... i−1])) is found (edge A). Further, since f(S1[j ... i])=f(S1[2 ... 3])=(00) and f(S2[j ... i])=f(S2[2 ... 3])=(01), the edge of E(f(S1[j ... i])) and E(f(S2 [j ... i])) is also found (edge A). Therefore, the decision at step 202 is again affirmative, and program control is shifted to step 232, whereat the parent node (the root node Vroot) of the edge of E(f(S1[j ... i])) and E(f(S2[j ... i])) is substituted into the parameter s. When the process at step 200 is performed the next time, the search is initiated beginning at the node that is stored in the parameter s. In addition, since the temporary t is φ, the decision at step 234 is affirmative, and the structure suffix tree generation process is temporarily terminated. When the value of the counter i is incremented, the structure suffix tree generation process is resumed under the condition wherein i=4 and j=2.

Since, with i=4 and j=2, f(S1[j ... i−1])=f(S1[2 ... 3])=(00) and f(S2[j ... i−1])=f(S2[2 ... 3])=(01), at step 200 the edge of E(f(S1[j ... i−1])) and E(f(S2[j ... i−1])) is found (edge A). Further, since f(S1[j ... i])=f(S1[2 ... 4])=(002) and f(S2[j ... i])=f(S2[2 ... 4])=(011), the edge of E(f(S1[j ... i])) and E(f(S2[j ... i])) is also present (edge A). Therefore, the decision at step 202 is again affirmative, and program control is shifted to step 232. The parent node (root node Vroot) of the edge of E(f(S1[j ... i])) and E(f(S2[j ... i])) is substituted into the parameter s. When the process at step 200 is performed next, the search is initiated beginning at the node that is stored in the parameter s. Furthermore, since the temporary t is φ, the decision at step 234 is affirmative, and the structure suffix tree generation process is temporarily terminated. When the value of the counter i is incremented, the structure suffix tree generation process is resumed under the condition wherein i=5 and j=2.

Since, with i=5 and j=2, f(S1[j ... i−1])=f(S1[2 ... 4])=(002) and f(S2[j ... i−1])=f(S2[2 ... 4])=(011), at step 200 the edge of E(f(S1[j ... i−1])) and E(f(S2[j ... i−1])) is found (edge A). In addition, since f(S1[j ... i])=f(S1[2 ... 5])=(0020) and f(S2[j ... i])=f(S2[2 ... 5])=(0110), the edge of E(f(S1[j ... i])) and E(f(S2[j ... i]))=φ and the node of V(f(S1[j . . . i−1])) and V(f(S2[j . . . i−1]))=φ. The decisions at steps 202 and 204 are negative, and program control is shifted to step 208.

At step 208, the edge of E(f(S1[j . . . i−1])) and E(f(S2[j . . . i−1])) (edge A in this case) is divided based on the search results obtained at step 200, and a node that corresponds to V(f(S1[j . . . i−1])) and V(f(S2[j . . . i−1])) is generated. Thus, as is shown in FIG. 6B, the edge A is divided into an edge (A1) having labels f(S1[j . . . i−1])=(002) and f(S2[j . . . i−1])=(011), and an edge (A2) having labels that are obtained by removing, from the original label, f(S1[j . . . i−1]) and f(S2[j . . . i−1]) (i.e., labels (2003$) and (1014$)). At step 210, "YES" is substituted into the flag node#constructed, and program control advances to step 212.

At this time, since the temporary t is φ, the decision at step 212 is affirmative, and program control is shifted to step 218. Since the flag node$constructed indicates "YES," the decision at step 218 is affirmative, and program control advances to step 222. At step 222, a node of V(f(S1[j . . . i−1])) and V(f(S2[j . . . i−1])) (a node between the edges A1 and A2 in this case) is stored in the temporary t. At step 224, the node stored in the area sL of the parent node (root node Vroot) of the node of V(f(S1[j . . . i−1])) and V(f(S2[j . . . i−1])) is substituted into the parameter s. When the process at step 200 is performed the next time, the search is initiated beginning at the node that is stored in the parameter s.

At step 226, a child node (leaf node) is prepared for the node between the edges A1 and A2. And a label (=(003$)) that is obtained by removing f(S[j . . . i−1])=f(S1[2 . . . 4]))=(002) from f(S1[j . . . ])=φ(S1[2 . . . ])=(002003$) (=(003$)), and a label (=(014$)) that is obtained by removing f(S2[j . . . i−1])= f(S2[2 . . . 4])=(011) from f(S2[j . . . ])=f(S2[2 . . . ])= (011014$) are provided for an edge B between the node between the edges A1 and A2 and the child node.

When the value of the counter j is incremented at step 228, i=5 and j=3 is obtained. Thus, the decision at step 230 is negative, and program control returns to step 200, whereat the structure suffix tree generation process is repeated under the condition wherein i=5 and j=3.

Since with i=5 and j=3, f(S1[j . . . i−1]) f(S1[3 . . . 4])=(00) and f(S2[j . . . i−1])=f(S2[3 . . . 4])=(01), at step 200 the edge of E(f(S1[j . . . i−1])) and E(f(S2[j . . . i−1])) is found (edge A1). Further, since f(S1[j . . . i])=f(S1[3 . . . 5])=(000) and f(S2[j . . . i])=f(S2[3 . . . 5])=(010), the edge of E(f(S1[j . . . i])) and E(f(S2[j . . . i]))=φ and the node of V(f(S1[j . . . i−1])) and V(f(S2[j . . . i−1]))=φ. The decisions at step 202 and 204 are negative, and program control advances to step 208.

At step 208, the edge (A1 in this case) of E(f(S1[j . . . i−1])) and E(f(S2[j . . . i−1])) is divided based on the search results obtained at step 200, and a node that corresponds to V(f(S1[j . . . i−1])) and V(f(S2[j . . . i−1])) is prepared. Thus, as is shown in FIG. 6C, the edge A1 is divided into an edge A3 having labels f(S1[j . . . i−1])=(00) and f(S2[j . . . i−1])=(01), and an edge A4 having labels ((2) and (1)) that are obtained by removing (f(S1[j . . . i−1]) and f(S2[j . . . i−1]) from the original label. At step 210, "YES" is substituted into the flag node#constructed, and program control advances to step 212.

At this time, since at step 222 the node between the old edge A1 (current edge A4) and the edge A2 is stored in the temporary t, the decision at step 212 is negative and program control advances to step 214. Then, the node of V(f(S1[j . . . i−1]) and V(f(S2[j . . . i−1]) (in this case, the node between the edges A3 and A4) is stored in the area sL of the node that is stored in the temporary t. At step 216, φ is substituted into the temporary t, and program control advances to step 218. Since the flag node#constructed indicates "YES," the decision at step 218 is affirmative, and program control advances to step 222.

At step 222, the node of V(f(S1[j . . . i−1])) and V(f(S2[j . . . i−1])) (the node between the edges A3 and A4 in this case) is stored in the temporary t. At step 224, a node that is stored in the area sL of the parent node (the root node Vroot) of the node of V(f(S1[j . . . i−1])) and V(f(S2[j . . . i−1])) is substituted into the parameter s. When the process at step 200 is performed the next time, the search is initiated beginning at the node that is stored in the parameter s.

At step 226, a child node (leaf node) is prepared for the node between the edges A3 and A4. Then, a label (=(003$)) that is obtained by removing f(S1[j . . . i−1])=f(S1[3 . . . 4])=(00) from f(S1[j . . . ])=f(S1[3 . . . ])=(00003$), and a label (=(014$)) that is obtained by removing f(S2[j . . . i−1])= f(S2[3 . . . 4])=(01) from f(S2[j . . . ])=f(S2[3 . . . ])=(00014$) are provided for an edge C between the node between the edges A3 and A4, and the child node.

When the value of the counter j is incremented at step 228, i=5 and j=4, and the decision at step 230 is negative. Program control thereafter returns to step 200, whereat the structure suffix tree generation process is repeated under the condition wherein i=5 and j=4.

Since, with i=5 and j=4, f(S1[j . . . i−1])=f(S1[4])=(0) and f(S2[j . . . i−1])=f(S2[4])=(0), at step 200 an edge A3 of E(f(S1[j . . . i−1]) and E(f(S2[j . . . i−1])) is found. Further, since f(S1[j . . . i])=f(S1[4 . . . 5])=(00) and f(S2[j . . . i])=f(S2[4 . . . 5])=(00), the edge of E(f(S1[j . . . i])) and E(f(S2[j . . . i]))=φ and the node of V(f(S1[j . . . i−1])) and V(f(S2[j . . . i−1]))=φ. Thus, the decisions at steps 202 and 204 are negative, and program control advances to step 208.

At step 208, the edge (A3 in this case) of E(f(S1[j . . . i−1])) and E(f(S2[j . . . i−1])) is divided based on the search results obtained at step 200, and a node that corresponds to V(f(S1[j . . . i−1])) and V(f(S2[j . . . i−1])) is prepared. Thus, as is shown in FIG. 6D, the edge A3 is divided into an edge A5 for which labels f(S1[j . . . i−1])=(0) and f(S2[j . . . i−1])=(0), and an edge A6 for which labels (i.e., (0) and (1)) that are obtained by removing f(S1 [j . . . i−1]) and f(S2[j . . . i−1]) from the original label. At step 210, "YES" is substituted into the flag node#constructed, and program control thereafter advances to step 212.

At this time, since at step 222 the node between the old edge A3 (current edge A6) and the edge A4 is stored in the temporary t, the decision at step 212 is negative, and program control advances to step 214. The node of V(f(S1[j . . . i−1])) and V(f(S2[j . . . i−1])) (the node between the edges A5 and A6 in this case) is stored in the area sL of the node that is stored in the temporary t. At step 216, φ is substituted into the temporary t, and program control advances to step 218. Since the flag node#constructed indicates "YES," the decision at step 218 is affirmative, and program control thereafter advances to step 222.

At step 222, the node of V(f(S1[j . . . i−1])) and V(f(S2 [j . . . i−1])) (the node between the edges A5 and A6) is stored in the temporary t. At step 224, a node that is stored in the area sL of the parent node (root node Vroot in this case) of the node of V(f(S1[j . . . i−1])) and V(f(S2[j . . . i−1])) is substituted into the parameter s. When the process at step 200 is performed the next time, the search is initiated beginning at the node that is stored in the parameter s.

At step 226, a child node (leaf nod) is prepared for the node between the edges A5 and A6. And a label (=(003$)) that is obtained by removing f(S1[j . . . i−1])=f(S1[4])=(0) from f(S1 [j . . . ])=f(S1[4 . . . ])=(0003$) and a label (=(010$)) that is obtained by removing f(S2[j . . . i−1])=(f(S2[4])=(0) from f(S2[j ... ])=f(S2[4 ... ])=(0010$) are provided for an edge D between the node between the edges A5 and A6 and the child node.

When the value of the counter j is incremented at step 228, i=5 and j=5, and the decision at step 230 is negative. Program control then returns to step 200, whereat the structure suffix tree generation process is repeated under the condition wherein i=5 and j=5.

While with i=j=5, S1[j ... i−1] and S2[j ... i−1]=φ and the edge of E(f(S1[j ... i−1])) and E(f(S2[j ... i−1]))=φ, S1[j ... i]=S1[5]=(0) and S2[j .... i]=S2[5]=(0), so that the edge (A5) of E(f(S1[j ... i])) and E(f(S2[j ... i])) is present. Thus, the decision at step 202 is affirmative, and program control is shifted to step 232. The parent node (the root node Vroot) of the edge of E(f(S1[j ... i])) and E(f(S2[j ... i])) is substituted into the parameter s. When the process at step 200 is performed the next time, the search is initiated beginning at the node that is stored in the parameter s.

At step 234, a check is performed to determine whether the temporary t is φ. Since at step 222 the node between the edges A5 and A6 is stored in the temporary t, the decision at step 234 is negative, and program control advances to step 236. The node (the root node Vroot in this case) that has been substituted into the parameter s is stored in the area sL of the node that is stored in the temporary t. At step 238, φ is substituted into the temporary t, and the structure suffix tree generation process is temporarily halted. When the value of the counter i is incremented, the structure suffix tree generation process is resumed under the condition wherein i=6 and j=5.

Since with i=6 and j=5, f(S1[j ... i−1])=f(S1[5])=(0) and f(S2[j ... i−1])=f(S2[5])=(0), at step 200 the edge (A5) of E(f(S1[j ... i−1]) and E(f(S2[j ... i−1])) is found. Further, since S1[j ... i]=S1[5 ... 6]=(00) and S2[j ... i]=S2[5 ... 6]=(01), the edge (A6) of E(f(S1[j ... i])) and E(f(S2[j ... i])) also exists. Therefore, the decision at step 202 is affirmative, and program control is shifted to step 232. The parent node (the node between the edges A5 and A6 in this case) of the edge of E(f(S1[j ... i])) and E(f(S2[j ... i])) is substituted into the parameter s. When the process at step 200 is performed the next time, the search is initiated beginning at the node that is stored in the parameter s.

Further, since φ is substituted into the temporary t, the decision at step 234 is affirmative, and the structure suffix tree generation process is temporarily halted. When the value of the counter i is incremented, the structure suffix tree generation process is resumed under the condition wherein i=7 and j=5.

Since, with i=7 and j=5, f(S1[j ... i−1])=f(S1[5 ... 6])=(00) and f(S2[j ... i−1])=f(S2[5 ... 6])=(01), at step 200 the edge (A6) of E(F(S1[j ... i−1])) and E(f(S2[j ... i−1])) is found. Further, since S1[j ... i]=S1[5 ... 7]=(000) and S2[j ... i]=S2[5 ... 7]=(010), the edge C of E(f(S1[j ... i])) and E(f(S2[j ... i])) is also present. Therefore, the decision at step 202 is affirmative, and program control is shifted to step 232. The parent node (the node between the edges A6 and C in this case) of the edge of E(f(S1[j ... i])) and E(f(S2[j ... i])) is substituted into the parameter s. When the process at step 200 is performed the next time, the search is initiated beginning at the node that is stored in the parameter s.

Since φ is substituted into the temporary t, the decision at step 234 is affirmative, and the structure suffix tree generation process is temporarily halted. When the value of the counter i is incremented, the structure suffix tree generation process is resumed under the condition wherein i=8 and j=5.

Since with i=8 and j=5, f(S1[j ... i−1])=f(S1[5 ... 7])=(000) and f(S2[j ... i−1])=f(S2[5 ... 7])=(010), at step 200 the edge C of E(f(S1[j ... i−1])) and E(f(S2[j ... i−1])) is found.

Furthermore, since f(S1[j ... i])=f(S1[5 ... 8])=(000$) and f(S2[j ... i])=f(S2[5 ... 8])=(010$), the edge of E(f(S1[j ... i])) and E(f(S2[j ... i]))=φ, and the node of V(f(S1[j ... i−1])) and V(f(S2[j ... i−1]))=φ. Thus, the decisions at steps 202 and 204 are negative, and program control advances to step 208.

At step 208, the edge (edge C in this case) of E(f(S1[j ... i−1])) and E(f(S2[j ... i−1])) is divided, and a node that corresponds to V(f(S1[j ... i−1])) and V(f(S2[j ... i−1])) is prepared. Thus, as is shown in FIG. 6E, the edge C is divided into an edge C1 having labels of f(S1[j ... i−1])=(0) and f(S2[j ... i−1])=(0), and an edge C2 having labels ((03$) and (14$)) that are obtained by removing f(S1[j ... i−1]) and f(S2[j ... i−1]) from the original label. At step 210, "YES" is substituted into the flag node#constructed, and program control advances to step 212.

Since the temporary t is φ at this time, the decision at step 212 is affirmative, and program control is shifted to step 218. Since the flag node#constructed indicates "YES," the decision at step 218 is affirmative, and program control advances to step 222. At step 222, the node (the node between the edges C1 and C2 in this case) of V(f(S1[j ... i−1])) and V(f(S2[j ... i−1])) is stored in the temporary t. At step 224, a node that is stored in the area sL of the parent node (the node between the edges A6 and C1 in this case) of the node of V(f(S1[j ... i−1])) and V(f(S2[j ... i−1])) is substituted into the parameter s. When the process at step 200 is performed the next time, the search is initiated beginning at the node that is stored in the parameter s.

At step 226, a child node (leaf node) is prepared for the node between the edges C1 and C2. Then, a label (=($)) that is obtained by removing f(S1[j ... i−1])=f(S1[5 ... 7])=(000) from f(S1[j ... ])=f(S1[5 ... ])=(000$), and a label (=($)) that is obtained by removing f(S2[j ... i−1])=f(S2[5 ... 7])=(010) from f(S2[j ... ])=f(S2[5 ... ])=(010$) are provided for an edge E between the node between the edges C1 and C2 and the child node. Through the above processing, for a range of j=1 to 5, the suffixes f(S1[j ... ]) and f(S2[j ... ]) of the first character string S1 and the second character string S2 are built in the structure suffix tree.

A brief explanation will now be given as for the range wherein j 6. For suffixes f(S1[6 ... ])=(00$) and f(S2[6 ... ])=(00$), as is shown in FIG. 6F, an edge D is divided into an edge D1 having labels of f(S1[j ... i−1])=f(S1[6])=(0) and f(S2[j ... i−1])=f(S2[6])=(0), and an edge D2 having labels (03$) and (10$) that are obtained by removing f(S1[j ... i−1]) and f(S2[j ... i−1]) from the original label. A child node is prepared between the edges D1 and D2. And a label (=($)) that is obtained by removing f(S1[j ... i−1])=f(S1[6 ... 7])=(00) from f(S1[j ... ])=f(S1[6 ... ])=(00$) and a label (=($)) that is obtained by removing f(S2[j ... i−1])=f(S2[6 ... 7])=(00) from f(S2[j ... ])=f(S2[6 ... ])=(000$) are provided for an edge F between the node between the edges D1 and D2 and the child node. As a result, the suffixes f(S1[6 ... ])=(00$) and f(S2[6 ... ])=(00$) are assembled into the structure suffix tree.

For suffixes f(S1[7 ... ])=(0$) and f(S2[7 ... ])=(0$), as is shown in FIG. 6G, a child node is prepared between the edges A5 and A6. And a label (=($)) that is obtained by removing f(S1[j ... i−1])=f(S1[7])=(0) from f(S1[j ... ])=f(S1[7 ... ])=(0$) and a label (=($)) that is obtained by removing f(S2[j ... i−1])=f(S2[7])=(0) from f(S2[j ... ])=f(S2[7 ... ])=(0$) are provided for an edge G between the node between the edges A5 and A6 and the child node. As a result, the suffixes f(S1[7 ... ])=(0$) and f(S2[7 ... ])=(0$) are assembled into the structure suffix tree.

Further, for suffixes f(S1 [8])=($) and f(S2[8])=($), as is shown in FIG. 6H, a child node is prepared for the root node. And a label of f(S1[j . . . ])=f(S1[8])=($) (f(S1[j . . . i−1])=φ) and a label of f(S2[j . . . ])=f(S2[8])=($) (f(S2[j . . . i−1])=φ) are provided for an edge H between the root node and the child node. As a result, the suffixes f(S1[8])=($) and f(S2[8])=($) are assembled into the structure suffix tree.

To make it easier to understand the structure suffix tree generation processing, an explanation has been given by employing a character string S that is much shorter than a character string that will actually be processed. Therefore, it is difficult to say that the area sL and the temporary t will function effectively. However, as the length of the character string and the scale of the suffix tree to be generated are increased, the area sL and the temporary t function more effectively, and the search at step 200 begins at a lower node based on the information stored in the area sL and the temporary t. Therefore, the time required to search for a node and to generate a structure suffix tree can be considerably reduced.

When the structure suffix tree for the target character string S is generated in the above described manner, the value of the counter i exceeds the value n, and the decision at step 110 is affirmative. The structure suffix tree generation processing is thereafter terminated.

An explanation will now be given for the analyzation of the structure of the character string S by using the structure suffix tree of the character string S (when the character string S represents a base array, the analyzation of the structure of the character string S is equivalent to the analyzation of the structure of the base array). The following processing is also implemented by the structure analyzation program that is installed in the computer system 10.

Sequences that are present in a single-stranded DNA base array or an RNA base array and that have the same structure tend to have similar functions. And when identical sequences or sequences that, even though their appearances differ, have the same structure appear frequently, the sequences may acquire a three-dimensional structure that induces an important function. Therefore, for the analyzation of genetic information, it is very important that sequences that have the same structure and that frequently appear in a single-stranded DNA base array or an RNA base array, including those sequences that have the same structure but that have different appearances, are regarded and extracted as identical sequences. On the other hand, through the following simple process, for which the structure suffix tree is used, all the character sequences that frequently appear in a character string S can be extracted, including the character sequences that have the same structure but that have different appearances.

That is, in the structure suffix tree, when a specific node V includes i leaf nodes as descendants (all the nodes present toward leaves as viewed from the node V), i character sequences of label(V) are present in the character string S (the same thing is applicable for the suffix tree). Therefore, a sequence that has a length of at least m and that appears at least i times can be extracted by searching all the nodes of the suffix tree that have at least i leaf nodes as descendants.

The above search method is the same as the method employed when frequently appearing character sequences are extracted from the suffix tree. When the structure suffix tree of the invention is employed for the search, all the sequences, including those that have the same structure but that have different appearances, can be extracted.

For the analyzation of genetic information, in addition to the above described extraction of frequently appearing sequences, it is also extremely important that the sequences that are present in the two base arrays be regarded and extracted as sequences having the same structure, regardless of whether these sequences have the same appearance. On the other hand, by employing the following simple process that uses the structure suffix tree, all the common character sequences that are present in the character string pair can be extracted, including the sequences that have the same structure but have different appearances.

Specifically, initially the character strings S1 and S2 (the first target array and the second target array), from which a common character sequence is to be extracted, are coupled together and the following character string S is obtained. S=S1+'$1'+S2+'$2' where + denotes coupling, $1 denotes a first end identification character (first identification data), and $2 denotes a second end identification character (second identification data). Then, the above described structure suffix tree generation process (the calculations performed for prev(S) and compl(S) and the generation of a structure suffix tree) is performed for the character string S that is employed as a processing target.

For the thus structured suffix tree, if a specific node V other than a leaf node has as descendants a leaf node V1 whose label(V) includes $1 and a leaf node V2 whose label(V2) does not include $1, it can be ascertained that the label(V) is a character sequence common to the character strings S1 and S2. Therefore, all the nodes that match the above condition are searched for and extracted from the structure suffix tree, so that all the character sequences common to the character strings S1 and S2 are extracted, including the sequences that have the same structure but have different appearances.

Through the calculations performed for prev(S) and compl(S) using the character string S, the first character string S1 and the second character string S2 that are obtained are regarded as a single pair of corresponding character strings, and a structure suffix tree is prepared wherein a label that corresponds to the character sequence of the first character string S1 and a label that corresponds to the character sequence of the second character string S2 are provided for the individual edges. Another method may also be used to generate the suffix tree.

Specifically, after the first character string S1 and the second character string S2 are obtained by performing the prev(S) and compl(S) calculations, all the "0"s that are present in one (defined as a character string A) of the character strings S1 and S2 are replaced with numerical values for which the signs of numerical values that are present at the same positions as the "0"s are inverted. Or, the character string may be replaced in accordance with an algorithm for directly changing the target character string into a character string that is obtained using the above described replacement process. Then, a single character string that is obtained may be employed to generate a structure suffix. In this case, since the amount of data for the character string that is provided as a label for each edge can be reduced, a smaller memory capacity will be required for the storage of the structure suffix tree.

Figure 5:
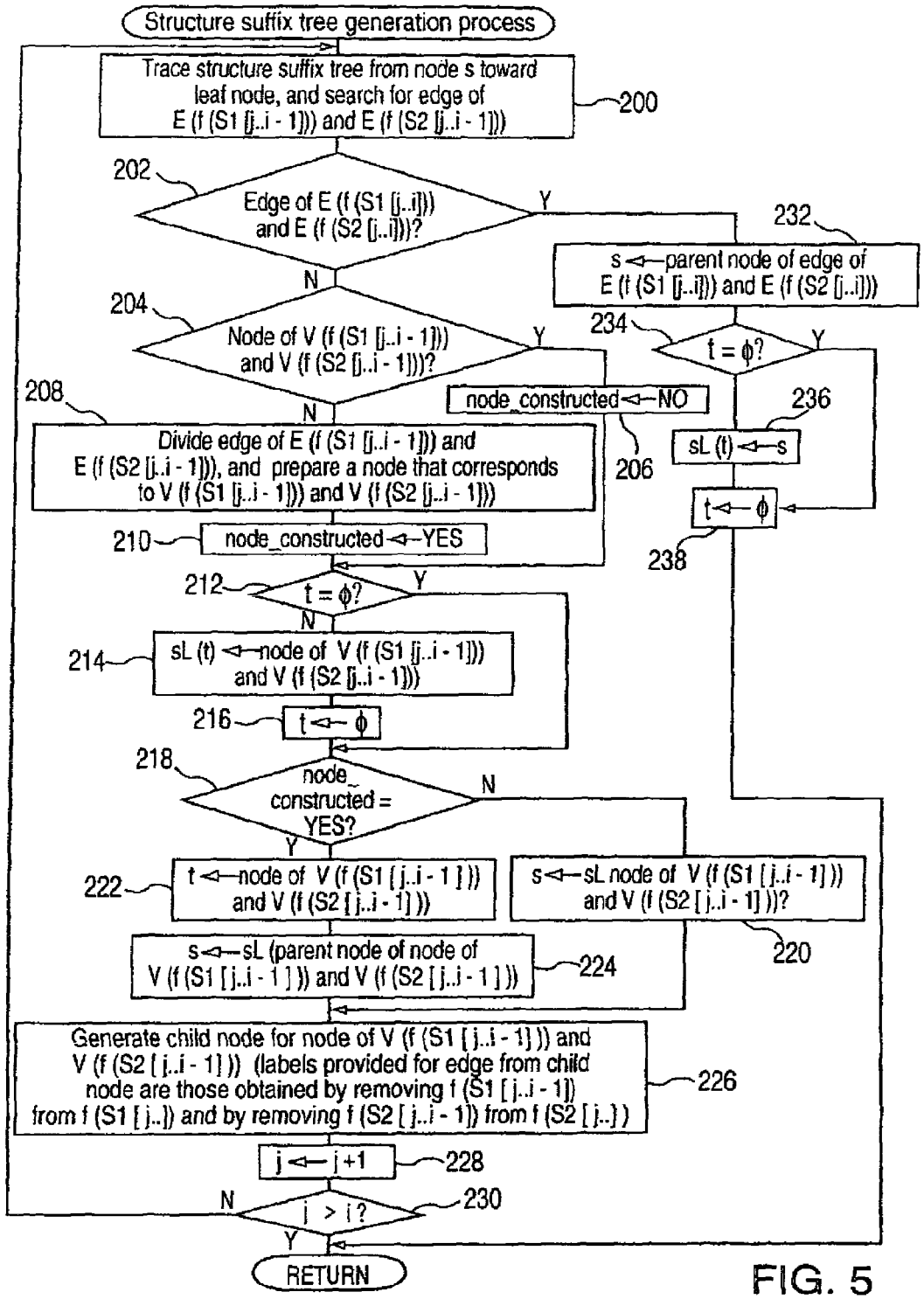
FIG. 5 is a flowchart showing the structure suffix tree generation processing.

Further, in the structure suffix tree generation process in FIG. 5, each time a new node other than a leaf node is generated (step 208) (i.e., each time "YES" is substituted into the flag node#constructed), the node of V(f(S1[j . . . i−1])) and V(f(S2[j . . . i−1])) is stored in the temporary t (step 222). Then, when the structure suffix tree generation process is performed the next time, the node of V(f(S1[j . . . i−1])) and V(f(S2[j . . . i−1])) (step 214), or a node that is substituted into the parameter s (step 236), is stored in the area sL of the node that is stored in the temporary t. The stored node is employed at step 200 to determine a node whereby the search for an edge is to be initiated. The invention, however, is not limited to this process, and a set T (with φ as the initial value) of nodes may be set for each edge of the structure suffix tree, and a node may be stored in the area sL by using the set T as follows.

Specifically, each time a new node other than a leaf node is prepared (step 208), all the nodes of the set T(e0) that corresponds to the edge (e0) of E(f(S1[j . . . i−1])) and E(f(S1[j . . . i−1])) are sorted in accordance with whether the value obtained by adding one to the length of the corresponding label is smaller than "i−2" or is greater than "i−1." Assume that of the two edges acquired by the edge division at step 208, an edge near the root node Vroot is defined as an edge e1, and an edge farther from the root node Vroot is defined as an edge e2. Of the nodes belonging to the set T(e0), the node whose label is ascertained to be shorter than "i−2" is allocated to the set T(e1) of the edge e1, while the node whose label is ascertained to be longer than "i−1" is allocated to the set T(e2) of the edge e2. For all the nodes v that are allocated to the set T(e2), the node of V(f(S1[j . . . i−1])) and V(f(S2[j . . . i−1])) is stored in the area sL(v). Then, at step 236, the node that is substituted into the parameter s is stored in the area sL of the node that is stored in the temporary t, and following this, the node that is stored in the temporary t is added to the set T(E(f(S1[j . . . i−1])) and E(f(S1[j . . . i−1]))).

Through the above processing, although the structure suffix tree generation process is slightly complicated, the search at step 200 can be initiated at a lower node, and the time required to search for a node and to generate a structure suffix tree can be further reduced.

The analyzation of the structure of a target array has been explained by using a character string that can be obtained by replacing the elements of the array with other characters. In this embodiment, arbitrary data can be used to replace the elements of the array, and an arbitrary data string that represents the target array can be employed to analyze the structure of the target array.

In the above description, the present invention has been applied for the analyzation of the structure of a DNA base array and an RNA base array. However, the present invention is not limited to such analyzations, and can also be applied for the analyzation of a similar polymer array structure.

In addition, in the above explanation, the structure analyzation program that carries out the array conversion method and the structure analyzation method of the invention is originally stored on the data storage medium 60, which is the storage medium that is employed in accordance with the present invention. Further, when the program on the data storage medium 60 is installed in the computer system 10 and executed, the computer system 10 functions as the structure analyzation apparatus of the invention. However, another mode may be employed. That is, the structure analyzation program may be retained in the storage device of another information processing apparatus (e.g., a network server) that is connected, across a computer network (e.g., a LAN, the Internet or a wireless communication network), to the computer system 10 via a public line or a communication medium (an optical fiber or a wireless line). When the computer system 10 communicates with the information processing apparatus, the program is transmitted from the information processing apparatus via the communication medium (the transmission medium of the invention) to the computer system 10. Then, the computer system 10 installs the received program in storage means, such as the HDD 40, and executes it, and can thus function as the structure analyzation apparatus of the present invention.

The experiments conducted by the present inventor will now be described.

First Embodiment

The following are all the HIV (Human Immunodeficiency Virus) RNA arrays (accession numbers of arrays: K03455; length: 9719).

```
tggaagggct aattcactcc caacgaagac aagatatcct
tgatctgtgg atctaccaca cacaaggcta cttccctgat
tagcagaact acacaccagg gccagggatc agatatccac
tgacctttgg atggtgctac aagctagtac cagttgagcc
agagaagtta gaagaagcca acaaaggaga gaacaccagc
ttgttacacc ctgtgagcct gcatggaatg gatgacccgg
agagagaagt gttagagtgg aggtttgaca gccgcctagc
atttcatcac atggcccgag agctgcatcc ggagtacttc
aagaactgct gacatcgagc ttgctacaag ggactttccg
ctggggactt tccagggagg cgtggcctgg gcgggactgg
ggagtggcga gccctcagat cctgcatata agcagctgct
ttttgcctgt actgggtctc tctggttaga ccagatctga
gcctgggagc tctctggcta actagggaac ccactgctta
agcctcaata agcttgcct tgagtgcttc aagtagtgtg
tgcccgtctg ttgtgtgact ctggtaacta gagatccctc
agacccttt agtcagtgtg gaaaatctct agcagtggcg
cccgaacagg gacctgaaag cgaaagggaa accagaggag
ctctctcgac gcaggactcg gcttgctgaa gcgcgcacgg
caagaggcga ggggcggcga ctggtgagta cgccaaaaat
tttgactagc ggaggctaga aggagagaga tgggtgcgag
agcgtcagta ttaagcgggg gagaattaga tcgatgggaa
aaaattcggt taaggccagg gggaaagaaa aaatataaat
taaaacatat agtatgggca agcagggagc tagaacgatt
cgcagttaat cctggcctgt tagaaacatc agaaggctgt
agacaaatac tgggacagct acaaccatcc cttcagacag
gatcagaaga acttagatca ttatataata cagtagcaac
cctctattgt gtgcatcaaa ggatagagat aaaagacacc
aaggaagctt tagacaagat agaggaagag caaaacaaaa
gtaagaaaaa agcacagcaa gcagcagctg acacaggaca
cagcaatcag gtcagccaaa attaccctat agtgcagaac
atccaggggc aaatggtaca tcaggccata tcacctagaa
ctttaaatgc atgggtaaaa gtagtagaag agaaggcttt
cagcccagaa gtgataccca tgttttcagc attatcagaa
ggagccaccc cacaagattt aaacaccatg ctaaacacag
tggggggaca tcaagcagcc atgcaaatgt taaaagagac
catcaatgag gaagctgcag aatgggatag agtgcatcca
gtgcatgcag ggcctattgc accaggccag atgagagaac
```

-continued

```
caaggggaag tgacatagca ggaactacta gtacccttca
ggaacaaata ggatggatga caaataatcc acctatccca
gtaggagaaa tttataaaag atggataatc ctgggattaa
ataaaatagt aagaatgtat agccctacca gcattctgga
cataagacaa ggaccaaagg aacccttag agactatgta
gaccggttct ataaaactct aagagccgag caagcttcac
aggaggtaaa aaattggatg acagaaacct tgttggtcca
aaatgcgaac ccagattgta agactatttt aaaagcattg
ggaccagcgg ctacactaga agaaatgatg acagcatgtc
agggagtagg aggacccggc cataaggcaa gagttttggc
tgaagcaatg agccaagtaa caaattcagc taccataatg
atgcagagag gcaatttag gaaccaaaga aagattgtta
agtgtttcaa ttgtggcaaa gaagggcaca cagccagaaa
ttgcagggcc cctaggaaaa agggctgttg gaaatgtgga
aaggaaggac accaaatgaa agattgtact gagagacagg
ctaatttttt agggaagatc tggccttcct acaagggaag
gccagggaat tttcttcaga gcagaccaga gccaacagcc
ccaccagaag agagcttcag gtctggggta gagacaacaa
ctcccccctca gaagcaggag ccgatagaca aggaactgta
tcctttaact tccctcaggt cactctttgg caacgacccc
tcgtcacaat aaagatagg ggcaactaa aggaagctct
attagataca ggagcagatg atacagtatt agaagaaatg
agtttgccag gaagatggaa accaaaaatg atagggggaa
ttggaggttt tatcaaagta agacagtatg atcagatact
catagaaatc tgtggacata agctataagg tacagtatta
gtaggaccta cacctgtcaa cataattgga agaaatctgt
tgactcagat tggttgcact ttaaattttc ccattagccc
tattgagact gtaccagtaa aattaaagcc aggaatggat
ggcccaaaag ttaaacaatg gccattgaca gaagaaaaaa
taaaagcatt agtagaaatt tgtacagaga tggaaaagga
agggaaaatt tcaaaattg ggcctgaaaa tccatacaat
actccagtat ttgccataaa gaaaaagac agtactaaat
ggagaaaatt agtagatttc agagaactta taagagaac
tcaagacttc tgggaagttc aattaggaat accacatccc
gcagggttaa aaagaaaaa atcagtaaca gtactggatg
tgggtgatgc atatttttca gttcccttag atgaagactt
caggaagtat actgcatta ccataccag tataaacaat
gagacaccag ggattagata tcagtacaat gtgcttccac
agggatggaa aggatcacca gcaatattcc aaagtagcat
gacaaaaatc ttagagcctt ttagaaaaca aaatccagac
```

```
atagttatct atcaatacat ggatgatttg tatgtaggat
ctgacttaga aatagggcag catagaacaa aaatagagga
gctgagacaa catctgttga ggtggggact taccacacca
gacaaaaaac atcagaaaga acctccattc ctttggatgg
gttatgaact ccatcctgat aaatggacag tacagcctat
agtgctgcca gaaaaagaca gctggactgt caatgacata
cagaagttag tggggaaatt gaattgggca agtcagattt
acccagggat taaagtaagg caattatgta aactccttag
aggaaccaaa gcactaacag aagtaatacc actaacagaa
gaagcagagc tagaactggc agaaaacaga gagattctaa
aagaaccagt acatggagtg tattatgacc catcaaaaga
cttaatagca gaaatacaga gcaggggca aggccaatgg
acatatcaaa tttatcaaga gccatttaaa aatctgaaaa
caggaaaata tgcaagaatg aggggtgccc acactaatga
tgtaaaacaa ttaacagagg cagtgcaaaa aataaccaca
gaaagcatag taatatgggg aaagactcct aaatttaaac
tgcccataca aaaggaaaca tgggaaacat ggtggacaga
gtattggcaa gccacctgga ttcctgagtg ggagtttgtt
aatacccctc ccttagtgaa attatggtac cagttagaga
aagaacccat agtaggagca gaaaccttct atgtagatgg
ggcagctaac agggagacta aattaggaaa agcaggatat
gttactaata gaggaagaca aaaagttgtc accctaactg
acacaacaaa tcagaagact gagttacaag caatttatct
agctttgcag gattcgggat tagaagtaaa catagtaaca
gactcacaat atgcattagg aatcattcaa gcacaaccag
atcaaagtga atcagagtta gtcaatcaaa taatagagca
gttaataaaa aaggaaaagg tctatctggc atgggtacca
gcacacaaag gaattggagg aaatgaacaa gtagataaat
tagtcagtgc tggaatcagg aaagtactat ttttagatgg
aatagataag gcccaagatg aacatgagaa atatcacagt
aattggagag caatggctag tgattttaac ctgccacctg
tagtagcaaa agaaatagta gccagctgtg ataaatgtca
gctaaaagga gaagccatgc atggacaagt agactgtagt
ccaggaatat ggcaactaga ttgtacacat ttagaaggaa
aagttatcct ggtagcagtt catgtagcca gtggatatat
agaagcagaa gttattccag cagaaacagg gcaggaaaca
gcatattttc ttttaaaatt agcaggaaga tggccagtaa
aaacaataca tactgacaat ggcagcaatt tcaccggtgc
tacggttagg gccgcctgtt ggtgggcggg aatcaagcag
gaatttggaa ttccctacaa tccccaaagt caaggagtag
tagaatctat gaataaagaa ttaaagaaaa ttataggaca
```

-continued

```
ggtaagagat caggctgaac atcttaagac agcagtacaa
atggcagtat tcatccacaa ttttaaaaga aaaggggggga
ttggggggta cagtgcaggg gaaagaatag tagacataat
agcaacagac atacaaacta aagaattaca aaaacaaatt
acaaaaattc aaaattttcg ggtttattac agggacagca
gaaatccact ttggaaagga ccagcaaagc tcctctggaa
aggtgaaggg gcagtagtaa tacaagataa tagtgacata
aaagtagtgc caagaagaaa agcaaagatc attagggatt
atggaaaaca gatggcaggt gatgattgtg tggcaagtag
acaggatgag gattagaaca tggaaaagtt tagtaaaaca
ccatatgtat gtttcaggga aagctagggg atggttttat
agacatcact atgaaagccc tcatccaaga ataagttcag
aagtacacat cccactaggg gatgctagat tggtaataac
aacatattgg ggtctgcata caggagaaaa agactggcat
ttgggtcagg gagtctccat agaatggagg aaaaagagat
atagcacaca agtagaccct gaactagcag accaactaat
tcatctgtat tactttgact gtttttcaga ctctgctata
agaaaggcct tattaggaca catagttagc cctaggtgtg
aatatcaagc aggacataac aaggtaggat ctctacaata
cttggcacta gcagcattaa taacaccaaa aaagataaag
ccacctttgc ctagtgttac gaaactgaca gaggatagat
ggaacaagcc ccagaagacc aagggccaca gagggagcca
cacaatgaat ggacactaga gcttttagag gagcttaaga
atgaagctgt tagacatttt cctaggattt ggctccatgg
cttagggcaa catatctatg aaacttatgg ggatacttgg
gcaggagtgg aagccataat aagaattctg caacaactgc
tgtttatcca ttttcagaat tgggtgtcga catagcagaa
taggcgttac tcgacagagg agagcaagaa atggagccag
tagatcctag actagagccc tggaagcatc caggaagtca
gcctaaaact gcttgtacca attgctattg taaaaagtgt
tgctttcatt gccaagtttg tttcataaca aaagccttag
gcatctccta tggcaggaag aagcggagac agcgacgaag
agctcatcag aacagtcaga ctcatcaagc ttctctatca
aagcagtaag tagtacatgt aacgcaacct ataccaatag
tagcaatagt agcattagta gtagcaataa taatagcaat
agttgtgtgg tccatagtaa tcatagaata taggaaaata
ttaagacaaa gaaaatagac aggttaatt gatagactaa
tagaaagagc agaagacagt ggcaatgaga gtgaaggaga
aatatcagca cttgtggaga tgggggtgga gatggggcac
catgctcctt gggatgttga tgatctgtag tgctacagaa
```

```
aaattgtggg tcacagtcta ttatggggta cctgtgtgga
aggaagcaac caccactcta ttttgtgcat cagatgctaa
agcatatgat acagaggtac ataatgtttg gccacacat
gcctgtgtac ccacagaccc caacccacaa gaagtagtat
tggtaaatgt gacagaaaat tttaacatgt ggaaaaatga
catggtagaa cagatgcatg aggatataat cagtttatgg
gatcaaagcc taaagccatg tgtaaaatta ccccactct
gtgttagttt aaagtgcact gatttgaaga atgatactaa
taccaatagt agtagcggga aatgataat ggagaaagga
gagataaaaa actgctcttt caatatcagc acaagcataa
gaggtaaggt gcagaaagaa tatgcatttt tttataaact
tgatataata ccaatagata atgatactac cagctataag
ttgacaagtt gtaacacctc agtcattaca caggcctgtc
caaaggtatc ctttgagcca attcccatac attattgtgc
cccggctggt tttgcgattc taaaatgtaa taataagacg
ttcaatggaa caggaccatg tacaaatgtc agcacagtac
aatgtacaca tggaattagg ccagtagtat caactcaact
gctgttaaat ggcagtctag cagaagaaga ggtagtaatt
agatctgtca atttcacgga caatgctaaa accataatag
tacagctgaa cacatctgta gaaattaatt gtacaagacc
caacaacaat acaagaaaaa gaatccgtat ccagagagga
ccagggagag catttgttac aataggaaaa ataggaaata
tgagacaagc acattgtaac attagtagag caaaatggaa
taacacttta aaacagatag ctagcaaatt aagagaacaa
tttggaaata ataaaacaat aatctttaag caatcctcag
gaggggaccc agaaattgta acgcacagtt ttaattgtgg
aggggaattt ttctactgta attcaacaca actgttaat
agtacttggt ttaatagtac ttggagtact gaagggtcaa
ataacactga aggaagtgac acaatcaccc tcccatgcag
aataaaacaa attataaaca tgtggcagaa agtaggaaaa
gcaatgtatg cccctcccat cagtggacaa attagatgtt
catcaaatat tacagggctg ctattaacaa gagatggtgg
taatagcaac aatgagtccg agatcttcag acctggagga
ggagatatga gggacaattg gagaagtgaa ttatataaat
ataaagtagt aaaaattgaa ccattaggag tagcacccac
caaggcaaag agaagagtgg tgcagagaga aaaaagagca
gtgggaatag gagctttgtt ccttgggttc ttgggagcag
caggaagcac tatgggcgca gcctcaatga cgctgacggt
acaggccaga caattattgt ctggtatagt gcagcagcag
aacaatttgc tgagggctat tgaggcgcaa cagcatctgt
tgcaactcac agtctggggc atcaagcagc tccaggcaag
```

-continued

```
aatcctggct gtggaaagat acctaaagga tcaacagctc ctggggattt ggggttgctc tggaaaactc atttgcacca ctgctgtgcc ttggaatgct agttggagta ataaatctct ggaacagatt tggaatcaca cgacctggat ggagtgggac agagaaatta acaattacac aagcttaata cactccttaa ttgaagaatc gcaaaaccag caagaaaaga atgaacaaga attattggaa ttagataaat gggcaagttt gtggaattgg tttaacataa caaattggct gtggtatata aaattattca taatgatagt aggaggcttg gtaggtttaa gaatagtttt tgctgtactt tctatagtga atagagttag gcagggatat tcaccattat cgtttcagac ccacctccca accccgaggg gacccgacag gcccgaagga atagaagaag aaggtggaga gagagacaga gacagatcca ttcgattagt gaacggatcc ttggcactta tctgggacga tctgcggagc ctgtgcctct tcagctacca ccgcttgaga gacttactct tgattgtaac gaggattgtg gaacttctgg gacgcagggg gtgggaagcc ctcaaatatt ggtggaatct cctacagtat tggagtcagg aactaaagaa tagtgctgtt agcttgctca atgccacagc catagcagta gctgagggga cagatagggt tatagaagta gtacaaggag cttgtagagc tattcgccac atacctagaa gaataagaca gggcttggaa aggattttgc tataagatgg gtggcaagtg gtcaaaaagt agtgtgattg gatggcctac tgtaagggaa agaatgagac gagctgagcc agcagcagat agggtgggag cagcatctcg agacctggaa aaacatggag caatcacaag tagcaataca gcagctacca atgctgcttg tgcctggcta gaagcacaag aggaggagga ggtgggtttt ccagtcacac ctcaggtacc tttaagacca atgacttaca aggcagctgt agatcttagc cacttttttaa aagaaaaggg gggactggaa gggctaattc actcccaaag aagacaagat atccttgatc tgtggatcta ccacacacaa ggctacttcc ctgattagca gaactacaca ccagggccag gggtcagata tccactgacc tttggatggt gctacaagct agtaccagtt gagccagata agatagaaga ggccaataaa ggagagaaca ccagcttgtt acaccctgtg agcctgcatg ggatggatga cccggagaga gaagtgttag agtggaggtt tgcagccgc ctagcatttc atcacgtggc ccgagagctg catccggagt acttcaagaa ctgctgacat cgagcttgct acaagggact ttccgctggg gactttccag ggaggcgtgg cctgggcggg actggggagt ggcgagccct cagatcctgc atataagcag ctgctttttg cctgtactgg gtctctctgg ttagaccaga
```

-continued

```
tctgagcctg ggagctctct ggctaactag ggaacccact gcttaagcct caataaagct tgccttgagt gcttcaagta gtgtgtgccc gtctgttgtg tgactctggt aactagagat ccctcagacc cttttagtca gtgtggaaaa tctctagca
```

For the above arrays, the present inventor employed the present invention to conduct an experiment in which a search was conducted for all patterns that had a length of at least 10 and that appeared at least three times. The search results are shown below.

```
===1st pattern: length = 10
   55: CCACACACAA
 9140: CCACACACAA
  238: GGAGAGAGAA
 9323: GGAGAGAGAA ===2nd pattern: length = 10
  259: GAGGTTTGAC
 9344: GAGGTTTGAC
  345: ACAAGGGACT
 9430: ACAAGGGACT ===3rd pattern: length = 10
  349: GGGACTTTCC
 9434: GGGACTTTCC
  363: GGGACTTTCC
 9448: GGGACTTTCC
 5131: TTTCAGGGAA ===4th pattern: length = 10
  294: CCCGAGACGT
 9379: CCCGAGAGCT
  622: AAATCTCTAG
 9707: AAATCTCTAG ===5th pattern: length = 10
  485: GGAGCTCTCT
 9570: GGAGCTCTCT
  676: GGAGCTCTCT ===6th pattern: length = 10
  227: ATGGATGACC
 9312: ATGGATGACC
  700: GCTTGCTGAA ===7th pattern: length = 10
   54: ACCACACACA
 9139: ACCACACACA
  780: AGGAGAGAGA ===8th pattern: length = 10
   26: AGACAAGATA
 9111: AGACAAGATA
 1092: AGACAAGATA ===9th pattern: length = 11
  274: CCTAGCATTTC
 9359: CCTAGCATTTC
 1345: CCATGCTAAAC ===10th pattern: length = 10
   13: TCACTCCCAA
 1739: GACAGAAACC
 9098: TCACTCCCAA ===11th pattern: length = 10
   93: CACCAGGGCC
 9178: CACCAGGGCC
 1849: GAGGACCCGG ===12th pattern: length = 10
 1948: GAAAGATTGT
 2057: GAAAGATTGT
 5591: AGGGAGCCAC
```

===13th pattern: length = 10
 343: CTACAAGGGA
9428: CTACAAGGGA
2108: CTACAAGGGA

===14th pattern: length = 10
 567: CTGTTGTGTG
9652: CTGTTGTGTG
2164: CAGAAGAGAG

===15th pattern: length = 10
 943: AAACATCAGA
3206: AAACATCAGA
2277: CCCTCGTCAC
7369: TTTCTACTGT ===16th pattern: length = 11
1817: AGAAGAAATGA
2350: AGAAGAAATGA
3962: ACAACAAATCA ===17th pattern: length = 10
 414: TCAGATCCTG
9499: TCAGATCCTG
2567: ACTGTACCAG ===18th pattern: length = 10
 515: GCTTAAGCCT
9600: GCTTAAGCCT
2617: ATGGCCATTG ===19th pattern: length = 10
 863: AAAGAAAAAA
2851: AAAGAAAAAA
2737: AAAGAAAAAA ===20th pattern: length = 10
 864: AAGAAAAAAT
2631: AAGAAAAAT
2852: AAGAAAAAT ===21st pattern: length = 10
2484: GACCTACACC
2873: CTGGATGTGG
4066: TCAAGCACAA ===22nd pattern: length = 10
 335: CTAGCTTGCT
9420: CGAGCTTGCT
3095: TACATGGATG ===23rd pattern: length = 10
2739: AGAAAAAGA
3201: ACAAAAAACA
7747: AGAAAAAGA ===24th pattern: length = 11
2276: CCCCTCGTCAC
3205: AAAACATCAGA
7368: TTTTCCTACTGT ===25th pattern: length = 11
 123: CCTTTGGATGG
9208: CCTTTGGATGG
3229: CCTTTGGATGG ===26th pattern: length = 11
 353: CTTTCCGCTGG
9438: CTTTCCGCTGG
3237: TGGGTTATGAA ===27th pattern: length = 10
 354: TTTCCGCTGG
9439: TTTCCGCTGG
3238: GGGTTATGAA ===28th pattern: length = 10
 405: GGCGAGCCCT
9490: GGCGAGCCCT
3383: TTATGTAAAC ===29th pattern: length = 10
3326: TTAGTGGGGA
3457: GGCAGAAAAC
3516: AATGAGGGGT ===30th pattern: length = 10
 554: AGTGTGTGCC
9639: AGTGTGTGCC
3466: CAGAGAGATT ===31st pattern: length = 10
 395: ACTGGGGAGT
9480: ACTGGGGAGT
3593: CTGAAAACAG ===32nd pattern: length = 10
2646: CATTAGTAGA
3633: CTAATGATGT
7219: CATTAGTAGA ===33rd pattern: length = 10
 611: GTCAGTGTGG
9696: GTCAGTGTGG
9001: CAGTCACACC
3956: ACTGACACAA ===34th pattern: length = 11
  86: AACTACACACC
9171: AACTACACACC
4157: CCAGCACACAA ===35th pattern: length = 10
 608: TTAGTCAGTG
9693: TTAGTCAGTG
4199: TTAGTCAGTG ===36th pattern: length = 10
  83: CAGAACTACA
9168: CAGAACTACA
4383: GACAAGTAGA ===37th pattern: length = 10
  65: GGCTACTTCC
9150: GGCTACTTCC
4538: TTAGCAGGAA ===38th pattern: length = 10
2895: TTTCAGTTCC
4665: AAAGTCAAGG
9080: GGGACTGGAA ===39th pattern: length = 10
4524: ATTTTCTTTT
4783: TAAAAGAAAA
9067: TAAAAGAAAA ===40th pattern: length = 10
 585: AACTAGAGAT
9670: AACTAGAGAT
5200: AAGTACACAT ===41st pattern: length = 10
 307: TCCGGAGTAC
9392: TCCGGAGTAC
5742: GAATTCTGCA ===42nd pattern: length = 11
 369: TTCCAGGGAGG
9454: TTCCAGGGAGG
5931: CCAAGTTTGTT ===43rd pattern: length = 10
 370: TCCAGGGAGG
9455: TCCAGGGAGG
5932: CAAGTTTGTT ===44th pattern: length = 10
3848: ATAGTAGGAG
5991: GCGACGAAGA
8285: ATAGTAGGAG

```
===45th pattern: length = 10
6078: AGTAGCAATA
6099: AGTAGCAATA
8928: AGTAGCAATA ===46th pattern: length = 10
  90: ACACACCAGG
9175: ACACACCAGG
6123: TGTGTGGTCC
7152: AGAGAGGACC ===47th pattern: length = 10
3601: AGGAAAATAT
5151: TGGTTTTATA
6251: AGGAAAATAT ===48th pattern: length = 10
1105: AAGAGCAAAA
6255: GGAGATGGGG
6267: GGAGATGGGG ===49th pattern: length = 10
3874: AGATGGGGCA
6269: AGATGGGGCA
7227: GAGCAAAATG ===50th pattern: length = 10
6047: AAGTAGTACA
6296: TTGATGATCT
8715: AAGTAGTACA ===51st pattern: length = 13
  42: ATCTGTGGATCTA
9127: ATCTGTGGATCTA
6409: TACAGAGGTACAT ===52nd pattern: length = 10
 235: CCCGGAGAGA
9320: CCCGGAGAGA
6429: GGGCCACACA ===53rd pattern: length = 11
 589: AGAGATCCCTC
9674: AGAGATCCCTC
6443: TGTGTACCCAC ===54th pattern: length = 10
 590: GAGATCCCTC
9675: GAGATCCCTC
6444: GTGTACCCAC ===55th pattern: length = 10
6294: TGTTGATGAT
8713: AGAAGTAGTA
6469: AGAAGTAGTA ===56th pattern: length = 10
 470: CCAGATCTGA
9555: CCAGATCTGA
6611: AAGTGCACTG ===57th pattern: length = 10
 182: AAAGGAGAGA
9267: AAAGGAGAGA
6674: AAAGGAGAGA ===58th pattern: length = 10
6070: ATACCAATAG
6639: ATACCAATAG
6767: ATACCAATAG ===59th pattern: length = 11
 418: ATCCTGCATAT
9503: ATCCTGCATAT
6787: TACCAGCTATA ===60th pattern: length = 10
 419: TCCTGCATAT
9504: TCCTGCATAT
6788: ACCAGCTATA ===61st pattern: length = 11
 121: GACCTTTGGAT
9206: GACCTTTGGAT
6837: GTCCAAGGTA ===62nd pattern: length = 10
 587: CTAGAGATCC
9672: CTAGAGATCC
6963: GTACACATGG ===63rd pattern: length = 10
 153: TTGAGCCAGA
7052: TTCACGGACA
9238: TTGAGCCAGA ===64th pattern: length = 10
  10: AATTCACTCC
9095: AATTCACTCC
7843: GGCCAGACAA ===65th pattern: length = 10
 356: TCCGCTGGGG
9441: TCCGCTGGGG
8310: GAATAGTTTT ===66th pattern: length = 10
6348: TACCTGTGTG
7148: ATCCAGAGAG
8532: GCTTGAGAGA ===67th pattern: length = 10
7965: TGGCTGTGGA
8542: CTTACTCTTG
8920: CAATCACAAG ===68th pattern: length = 10
 115: TCCACTGACC
9200: TCCACTGACC
8630: TGGAGTCAGG ===69th pattern: length = 10
 550: AAGTAGTGTG
9635: AAGTAGTGTG
8816: AAGTAGTGTG ===70th pattern: length = 10
 188: GAGAACACCA
9273: GAGAACACCA
8974: CACAAGAGGA ===71st pattern: length = 10
8422: AGAAGAAGAA
8979: GAGGAGGAGG
8982: GAGGAGGAGG ===72nd pattern: length = 11
 611: GTCAGTGTGGA
9696: GTCAGTGTGGA
9001: CAGTCACACCT ===73rd pattern: length = 10
 612: TCAGTGTGGA
9697: TCAGTGTGGA
9002: AGTCACACCT
```

Of the 73 patterns that were found in the course of the application of the first embodiment, 22 patterns were repetitive patterns, which generally were found to have a common suffix tree, while the remaining 51 patterns were patterns that it was doubtful would have been discovered had the present invention not been employed.

Second Embodiment

Using the same arrays as those used for the first embodiment, the present inventor employed the present invention to conduct an experiment in which a search was conducted for all the patterns that had a length of at least 8 and that appeared at least 7 times. The search results are shown below.

```
===1st pattern: length = 8
   54: ACCACACA
 9139: ACCACACA
  780: AGGAGAGA
  184: AGGAGAGA
 9269: AGGAGAGA
 6121: GTTGTGTG
  569: GTTGTGTG
 9654: GTTGTGTG
 2166: GAAGAGAG
 6676: AGGAGAGA ===2nd pattern: length = 8
   58: CACACAAG
 9143: CACACAAG
 1472: GAGAGAAC
 6352: TGTGTGGA
  186: GAGAGAAC
 9271: GAGAGAAC
 5324: CACACAAG ===3rd pattern: length = 8
   91: CACACCAG
 9176: CACACCAG
  160: AGAGAAGT
 6124: GTGTGGTC
 7153: GAGAGGAC
  242: AGAGAAGT
 9327: AGAGAAGT
 3193: CACACCAG
 7385: ACACAACT ===4th pattern: length = 8
   71: TTCCCTGA
 9156: TTCCCTGA
  261: GGTTTGAC
 9346: GGTTTGAC
  347: AAGGGACT
 9432: AAGGGACT
 5280: TTGGGTCA ===5th pattern: length = 8
   99: GGCCAGGG
 2119: GGCCAGGG
  383: GGCCTGGG
 9468: GGCCTGGG
  853: GGCCAGGG
 4885: AATTCAAA
 9184: GGCCAGGG ===6th pattern: length = 8
  296: CGAGAGCT
 9381: CGAGAGCT
  588: TAGAGATC
 9673: TAGAGATC
 6964: TACACATG
  624: ATCTCTAG
 9709: ATCTCTAG ===7th pattern: length = 8
  508: ACCCACTG
 9593: ACCCACTG
  594: TCCCTCAG
 9679: TCCCTCAG
 3699: GAAAGACT
 5287: AGGGAGTV
 2250: TCCCTCAG ===8th pattern: length = 8
  411: CCCTCAGA
 9496: CCCTCAGA
  595: CCCTCAGA
 9680: CCCTCAGA
 2204: CCCTCAGA
 3700: AAAGACTC
 5288: GGGAGTCT ===9th pattern: length = 8
   56: CACACA
 9141: VSVSVSVS
  239: GAGAGAGA
 9324: GAGAGAGA
  782: GAGAGAGA
 8436: GAGAGAGA
 8437: AGAGAGAG
 8438: GAGAGAGA ===10th pattern: length = 8
  227: ATGGATGA
 9312: ATGGATGA
  700: GCTTGCTG
 1532: ATGGATGA
  897: GCAAGCAG
 1136: GCAAGCAG
 3098: ATGGATGA ===11th pattern: length = 8
  630: AGCAGTGG
  946: CATCAGAA
 1535: GATGACAA
 7887: TGCTGAGG
 3209: CATCAGAA
 7756: AGCAGTGG
 6004: CATCAGAA ===12th pattern: length = 8
  398: GGGGAGTG
 9483: GGGGAGTG
 1070: AAAAGACA
 3462: AAAACAGA
 6591: CCCCACTC
 2743: AAAAGACA
 3292: AAAAGACA
 5044: AAAACAGA
 7249: AAAACAGA ===13th pattern: length = 8
  786: GAGATGGG
 1106: AGAGCAAA
 6256: GAGATGGG
 6268: GAGATGGG
 7226: AGAGCAAA
 2832: CACATCCC
 5205: CACATCCC ===14th pattern: length = 8
  863: AAAGAAAA
 2851: AAAGAAAA
 2737: AAAGAAAA
 6167: AAAGAAAA
 1112: AAACAAAA
 3065: AAACAAAA
 4526: TTTCTTTT
 4702: AAAGAAAA
 4785: AAAGAAAA
 9069: AAAGAAAA ===15th pattern: length = 8
  865: AGAAAAAA
 2632: AGAAAAAA
 2853: AGAAAAAA
 1123: AGAAAAAA
 2739: AGAAAAAA
 3201: ACAAAAAA
 7747: AGAAAAAA
 1359: GTGGGGGG ===16th pattern: length = 8
 1258: AAGTAGTA
 8868: CCAGCAGC
 1502: AACTACTA
 6047: AAGTAGTA
 6296: TTGATGAT
 8715: AAGTAGTA
 6471: AAGTAGTA
 7683: AAGTAGTA ===17th pattern: length = 8
  294: CCCGAGAG
 9379: CCCGAGAG
  622: AAATCTCT
 9707: AAATCTCT
```

```
-continued
 1665: TTTAGAGA
 8072: AAATCTCT
 1983: GGGCACAC

===18th pattern: length = 8
  756: AAATTTTG
 1787: TTTAAAAG
 2005: GGGCCCCT
 4891: AAATTTTC
 2542: AAATTTTC
 4781: TTTAAAAG
 9065: TTTAAAAG
 7246: TTTAAAAC ===19th pattern: length = 8
  259: GAGGTTTG
 9344: GAGGTTTG
  345: ACAAGGGA
 9430: ACAAGGGA
 2035: GTGGAAAG
 2110: ACAAGGGA
 3841: AGAACCCA
 7970: GTGGAAAG ===20th pattern: length = 8
  566: TCTGTTGT
 9651: TCTGTTGT
 2191: AGACAACA
 3434: ACAGAAGA
 2627: ACAGAAGA
 3164: AGACAACA
 7734: GAGTGGTG ===21st pattern: length = 8
  169: AGAAGAAG
 3436: AGAAGAAG
 2193: ACAACAAC
 7021: AGAAGAAG
 7635: GAGGAGGA
 8422: AGAAGAAG
 8979: GAGGAGGA
 8982: GAGGAGGA
 8425: AGAAGAAG ===22nd pattern: length = 8
 1358: AGTGGGGG
 3200: GACAAAAA
 2199: ACTCCCCC
 3288: CAGAAAAA
 3040: GACAAAAA
 6315: CAGAAAAA
 3936: GACAAAAA
 5378: CTGTTTTT ===23rd pattern: length = 8
 1915: TAATGATG
 2476: ATTAGTAG
 2647: ATTAGTAG
 2767: ATTAGTAG
 3634: TAATGATG
 7220: ATTAGTAG
 6093: ATTAGTAG ===24th pattern: length = 8
 1124: GAAAAAAG
 4792: AGGGGGGA
 4801: TGGGGGGT
 2740: GAAAAAAG
 3202: CAAAAAAC
 7748: GAAAAAAG
 9076: AGGGGGGA ===25th pattern: length = 8
 2036: TGGAAAGG
 2111: CAAGGGAA
 3005: TGGAAAGG
 8775: TGGAAAGG
 4931: TGGAAAGG
 2111: CAAGGGAA
 4955: TGGAAAGG
 7781: CTTGGGTT ===26th pattern: length = 8
  864: AAGAAAAA
 2631: AAGAAAAA
 2852: AAGAAAAA
 1122: AAGAAAAA
 2738: AAGAAAAA
 3145: AACAAAAA
 6168: AAGAAAAA
 7132: AAGAAAAA ===27th pattern: length = 8
 2128: ATTTTCTT
 2157: GCCCCACC
 3477: TAAAAGAA
 3642: TAAAACAA
 7291: TAAAACAA
 4524: ATTTTCTT
 4783: TAAAAGAA
 9067: TAAAAGAA
 7482: TAAAACAA
 7529: GCCCCTCC ===28th pattern: length = 8
  373: AGGGAGGC
 9458: AGGGAGGC
 4820: GAAAGAAT
 6733: GAAAGAAT
 3793: GTTTGTTA
 8797: TGGGTGGC
 8847: GAAAGAAT ===29th pattern: length = 8
 1111: AAAACAAA
 2850: AAAAGAAA
 3064: AAAACAAA
 4525: TTTTCTTT
 4784: AAAAGAAA
 9068: AAAAGAAA
 3804: CCCCTCCC
 4327: AAAAGAAA
 4870: AAAACAAA
 7483: AAAACAAA
 7530: CCCCTCCC
 8587: GGGGTGGG ===30th pattern: length = 8
  587: CTAGAGAT
 9672: CTAGAGAT
 6963: GTACACAT
 4422: GTACACAT
 6576: CATGTGTA
 5202: GTACACAT
 5467: GATCTCTA ===31st pattern: length = 8
  282: TTCATCAC
  550: AAGTAGTG
 9635: AAGTAGTG
 8816: AAGTAGTG
 4496: CCAGCAGA
 5001: AAGTAGTG
 9367: TTCATCAC ===32nd pattern: length = 8
  755: AAAATTTT
 1786: TTTTAAAA
 4890: AAAATTTT
 4780: TTTTAAAA
 9064: TTTTAAAA
 4530: TTTTAAAA
 6495: AAAATTTT ===33rd pattern: length = 8
  374: GGGAGGCG
 9459: GGGAGGCG
 4560: AAACAATA
 4821: AAAGAATA
 8644: AAAGAATA
 6734: AAAGAATA
 7293: AAACAATA
```

-continued

```
===34th pattern: length = 8
  1324: CCACCCCA
  8181: AAGAAAAG
  4786: AAGAAAAG
  9070: AAGAAAAG
  7358: GGAGGGGA
  5014: AAGAAAAG
  7319: GGAGGGGA ===35th pattern: length = 8
  2788: TAATAAGA
  5497: TAATAACA
  6870: ATTATTGT
  5233: TAATAACA
  5736: TAATAAGA
  6910: TAATAAGA
  7852: ATTATTGT ===36th pattern: length = 8
  6368: ACCACCAC
  7022: GAAGAAGA
  7636: AGGAGGAG
  7120: CAACAACA
  8423: GAAGAAGA
  8980: AGGAGGAG
  8983: AGGAGGAG ===37th pattern: length = 8
    84: AGAACTAC
  9169: AGAACTAC
  4186: ACAAGTAG
  4384: ACAAGTAG
  5327: ACAAGTAG
  7556: TGTTCATC
  8925: ACAAGTAG
```

Third Embodiment

The following are arrays (access number: SA16SRRNA, length: 1334) for the 16S portion of Streptococcus anginosus bacteria.

gaacgggtgagtaacgcgtaggtaacctgcctattagagggggataacta ttggaaacgatagctaataccgcataacagtatgtaacacatgttagatg cttgaaagatgcaattgcatcgctagtagatggacctgcgttgtattagc tagtaggtagggtaaaggcctacctaggcactcctacgggaggcagcagt agggaatcttcggcaatgggggaaccctgaccgagcaacgccgcgtgag tgaagaaggttttcggatcgtaaagctctgttgttaaggaagaacgagtg tgagaatggaaagttcatactgtgacggtacttaaccagaaagggacggc tnactacgtgccagcagccgcggtaatacgtaggtcccnagcgttgtccg gatttattgggcgtaaagcgagcgcaggcggttagaaaagtctgaagtga aaggcagtggctcaaccattgtaggctttggaaactgtttaacttgagtg cagaaggggagagtggaattccatgtgtagcggtgaaatgcgtagatata tggaggaacaccggtggcgaaagcggctctctggtctgtaactgacgctg aggctcgaaagcgtggggagcgaacaggattagataccctngtagtccac gccgtaaacgatgagtgctaggtgttgggtccttccgggactcagtgcc gcagctaacgcattaagcactccgcctggggagtacgaccgcaaggttga aactcaaaggaattgacgggggccgcacaagcggtggagcatgtngttta attcgaagnaacgcgaagaaccttaccaggtcttgacatcccgatgctnt ttctagagataggaagtttcttcggaacatcggtgacaggtggtgaatgg ttgtcgtcagctcgtgtcgtgagatgttgggttaagtcccgcaacgagcg caaccctnattgttagttgccatcattaagttgggcactctagcgagact gccggtaatnaaccggaggaaggtggggatgacgtcaaatcatcatgccc cttatgacctnggctacacacgtgctacaatggctggtacaacgagtcgc aagccggtgacggcaagctaatctctgaaagccagtctcagttcggattg taggctgcaactcgcctncatgaagtcggaatcgctagtaatcgcggatc agcacgccgcggtgaatacgttcccgggccttgtacacaccgcncgtcac accacgagagtttgtaacaccccga For the above arrays, the present inventor employed the present invention to conduct an experiment in which a search was conducted for all the patterns that had a length of at least 10 and that appeared at least two times. The search results are shown below. Since the arrays searched for in the third embodiment were shorter than those in the first or the second embodiment, a reduced number of patterns were found.

```
===1st pattern: length = 10
  131: GGACCTGCGT
  370" AAGTTCATAC

===2nd pattern: length = 10
   97: ATGCTTGAAA
  438: CGTAGGTCCC

===3rd pattern: length = 11
  280: GGGAACCCTGA
  536: TTTGGAAACTG

===4th pattern: length = 10
   29: CCTATTAGAG
  630: AAGCGGCTCT

===5th pattern: length = 10
  739: TCCTTTCCGG
  985: GTTGGGTTAA

===6th pattern: length = 10
  527: ATTGTAGGCT
 1206: ATTGTAGGCT

===7th pattern: length = 10
  118: ATCGCTAGTA
 1240: ATCGCTAGTA
```

As is described above, according to the present invention, for a variable in a target array that can be replaced by another element in the array, information is substituted that indicates the location of a different variable that forms a complementary pair with the variable that can be replaced, or, for a variable in the target array for which no different, complementary variable is available, information is substituted indicating that no such variable is available. Since to change an array this process is performed for all the variables therein, the present invention can provide an excellent effect by so altering an array that its structure can be efficiently analyzed.

Further, according to the present invention, for a variable in a target array that can be replaced by another element, information is substituted that indicates the location of a like variable, or, for a variable in the target array for which a like variable is not available, information is substituted indicating that no like variable is available in order to change the target array into a first array.

Furthermore, for a variable in a target array that can be replaced by another element, information is substituted that indicates the location of a different variable that forms a complementary pair with the variable that can be replaced, or, for a variable in the target array for which a different, complementary variable is not available, information is substituted indicating that no such variable is available in order to change the target array into a second array. Then, since the first and the second arrays are employed to analyze the structure of the target array, the present invention can provide an excellent effect whereby the structure of the target array can be efficiently analyzed.

While the invention has been particularly shown and described with respect to preferred embodiments thereof, it will be understood by those skilled in the art that the foregoing and other changes in form and details may be made therein without departing form the spirit and scope of the invention.

Having thus described my invention what I claim as new, and desire to secure by Letters Patent is:

1. A method for changing a character string that represents a DNA or RNA base array comprised of a multitude of nucleotides, said character string including a sequence of characters, each of said characters representing one of the nucleotides of the DNA or RNA base array, wherein said characters include one or more pairs of characters that are complementary to each other, the method comprising the steps of:

traversing the character string in a defined order;

for each of at least selected ones of said characters in the character string, if the character string includes, earlier in the character string in said defined order than said each character, a complementary character of said each character, then changing said each character to information that represents the location in said array of the complementary character of said each character, and if said each character does not have a complementary character in the character string, earlier in the array, in said defined order, than said each character, then changing said each character to information indicating that there is no complementary character of said each character in said character string, earlier in the array, in said defined order, than said each character; and using a computer system including one or more processor units, executing a character string transformation program, to perform the changing steps.

2. An article of manufacture comprising:

at least one tangible computer readable medium having computer readable program code logic to execute machine instructions in one or more processing units for transforming a target array that represents a DNA or RNA base array comprised of a multitude of nucleotides, said target array including a sequence of character, each of said characters representing one of the nucleotides of the DNA or RNA base array, wherein complementary some of the characters in the target array are complementary to others of the characters of the target array, said computer readable program code logic, when executing, performing the following:

converting the target array into a first array by changing each of at least selected ones of the characters in said target array into information representing the location of the same character in the target array, when said target array is viewed along a path extending in a predetermined direction, and when said same character is present upstream of said each character, and by changing said each character, when said same character is not present upstream of said each character in said target array, into information indicating that said same character is not present in the target array upstream of said each character;

changing said target array into a second array by changing each of at least selected ones of the characters in the target array into information representing the location of the character in the target array that is complementary to said each character when said target array is viewed along a path extending in a predetermined direction, and when a character that is complementary to said each character is present upstream of said each character, and by changing, when said complementary character is not present upstream of said each character in said target array, into information indicating that said complementary character is not present in the target array upstream of said each character; and employing said first and said second arrays to analyze the structure of said target array.

3. The method according to claim 1, wherein said target array is changed to a first and a second arrays by using, as information that indicates the position of the different variable or the position of said same variable, numerical information that represents the number of elements arranged in said target array beginning at the position of a target variable and continuing up to the position of said same variable, or said different variable;

wherein, for said first and said second thus obtained arrays, all of said information indicating that said different variable or said same variable is not present in said target array is replaced with numerical information, obtained by inverting the positive and negative signs of said numerical information, indicating the number of elements that are present in another array at locations corresponding to said information;

wherein a suffix tree is prepared by regarding the obtained array as a character string; and wherein, among the sequences of said obtained array that are provided as labels for edges of said suffix tree, numerical information indicating the positioning of said same variable or said different variable that is not present in each of said sequences is replaced with information indicating that said same variable or said different variable is not present; and wherein said suffix tree is employed to analyze the structure of said target array.

4. The method according to claim 3, wherein said suffix tree is employed to extract a sequence that has the same structure and that frequently appears in said target array, so that said structure of said target array is analyzed.

5. The method according to claim 4, wherein said target array is an array where said first target array, first identification information, said second target array, first identification information, said second target array and second identification information are arranged in order; and wherein, when said suffix tree is employed to search for said common sequence for said first and said second arrays, said structures of said first array and said second array are analyzed.

* * * * *

SEQUENCE LISTING

```
<160> NUMBER OF SEQ ID NOS: 2

<210> SEQ ID NO 1
<211> LENGTH: 9719
<212> TYPE: DNA
<213> ORGANISM: Human iImmunodeficiency virus type 1

<400> SEQUENCE: 1
tggaagggct aattcactcc caacgaagac aagatatcct tgatctgtgg atctaccaca      60
cacaaggcta cttccctgat tagcagaact acacaccagg gccagggatc agatatccac     120
tgacctttgg atggtgctac aagctagtac cagttgagcc agagaagtta gaagaagcca     180
acaaaggaga gaacaccagc ttgttacacc ctgtgagcct gcatggaatg gatgacccgg     240
agagagaagt gttagagtgg aggtttgaca gccgcctagc atttcatcac atggcccgag     300
agctgcatcc ggagtacttc aagaactgct gacatcgagc ttgctacaag ggactttccg     360
ctggggactt tccagggagg cgtggcctgg gcgggactgg ggagtggcga gccctcagat     420
cctgcatata agcagctgct ttttgcctgt actgggtctc tctggttaga ccagatctga     480
gcctgggagc tctctggcta actagggaac ccactgctta agcctcaata agcttgcct      540 tgagtgcttc aagtagtgtg tgcccgtctg ttgtgtgact ctggtaacta gagatccctc     600 agacccttt agtcagtgtg gaaaatctct agcagtggcg cccgaacagg gacctgaaag     660
cgaaagggaa accagaggag ctctctcgac gcaggactcg gcttgctgaa gcgcgcacgg     720
caagaggcga ggggcggcga ctggtgagta cgccaaaaat tttgactagc ggaggctaga     780
aggagagaga tgggtgcgag agcgtcagta ttaagcgggg gagaattaga tcgatgggaa     840
aaaattcggt taaggccagg gggaaagaaa aaatataaat taaaacatat agtatgggca     900
agcagggagc tagaacgatt cgcagttaat cctggcctgt tagaaacatc agaaggctgt     960
agacaaatac tgggacagct acaaccatcc cttcagacag gatcagaaga acttagatca    1020
ttatataata cagtagcaac cctctattgt gtgcatcaaa ggatagagat aaaagacacc    1080
aaggaagctt tagacaagat agaggaagag caaaacaaaa gtaagaaaaa agcacagcaa    1140
gcagcagctg acacaggaca cagcaatcag gtcagccaaa attaccctat agtgcagaac    1200
atccaggggc aaatggtaca tcaggccata tcacctagaa ctttaaatgc atgggtaaaa    1260
gtagtagaag agaaggcttt cagcccagaa gtgataccca tgttttcagc attatcagaa    1320
ggagccaccc cacaagattt aaacaccatg ctaaacacag tggggggaca tcaagcagcc    1380
atgcaaatgt taaaagagac catcaatgag gaagctgcag aatgggatag agtgcatcca    1440
gtgcatgcag ggcctattgc accaggccag atgagagaac caaggggaag tgacatagca    1500
ggaactacta gtacccttca ggaacaaata ggatggatga caaataatcc acctatccca    1560
gtaggagaaa tttataaaag atggataatc ctgggattaa ataaaatagt aagaatgtat    1620
agccctacca gcattctgga cataagacaa ggaccaaagg aacccttag agactatgta     1680
```

```
gaccggttct ataaaactct aagagccgag caagcttcac aggaggtaaa aaattggatg    1740
acagaaacct tgttggtcca aaatgcgaac ccagattgta agactatttt aaaagcattg    1800
ggaccagcgg ctacactaga agaaatgatg acagcatgtc agggagtagg aggacccggc    1860
cataaggcaa gagttttggc tgaagcaatg agccaagtaa caaattcagc taccataatg    1920
atgcagagag gcaattttag gaaccaaaga aagattgtta agtgtttcaa ttgtggcaaa    1980
gaagggcaca cagccagaaa ttgcagggcc cctaggaaaa agggctgttg gaaatgtgga    2040
aaggaaggac accaaatgaa agattgtact gagagacagg ctaattttt agggaagatc     2100 tggccttcct acaagggaag gccagggaat tttcttcaga gcagaccaga gccaacagcc    2160
ccaccagaag agagcttcag gtctggggta gagacaacaa ctcccccctca gaagcaggag   2220 ccgatagaca aggaactgta tcctttaact tccctcaggt cactctttgg caacgacccc    2280
tcgtcacaat aaagatagg gggcaactaa aggaagctct attagataca ggagcagatg     2340
atacagtatt agaagaaatg agtttgccag gaagatggaa accaaaaatg ataggggga    2400 ttggaggttt tatcaaagta agacagtatg atcagatact catagaaatc tgtggacata    2460
aagctatagg tacagtatta gtaggaccta cacctgtcaa cataattgga agaaatctgt    2520
tgactcagat tggttgcact ttaaattttc ccattagccc tattgagact gtaccagtaa    2580
aattaaagcc aggaatggat ggcccaaaag ttaaacaatg gccattgaca gaagaaaaaa   2640
taaaagcatt agtagaaatt tgtacagaga tggaaaagga agggaaaatt tcaaaaattg    2700
ggcctgaaaa tccatacaat actccagtat ttgccataaa gaaaaaagac agtactaaat    2760
ggagaaaatt agtagatttc agagaactta ataagagaac tcaagacttc tgggaagttc    2820
aattaggaat accacatccc gcagggttaa aaagaaaaa atcagtaaca gtactggatg    2880
tgggtgatgc atattttca gttcccttag atgaagactt caggaagtat actgcattta    2940
ccatacctag tataaacaat gagacaccag ggattagata tcagtacaat gtgcttccac    3000
agggatggaa aggatcacca gcaatattcc aaagtagcat gacaaaaatc ttagagcctt    3060
ttagaaaaca aaatccagac atagttatct atcaatacat ggatgatttg tatgtaggat    3120
ctgacttaga aatagggcag catagaacaa aaatagagga gctgagacaa catctgttga    3180
ggtggggact taccacacca gacaaaaaac atcagaaaga acctccattc ctttggatgg    3240
gttatgaact ccatcctgat aaatggacag tacagcctat agtgctgcca gaaaaagaca    3300
gctggactgt caatgacata cagaagttag tggggaaatt gaattgggca agtcagattt    3360
acccagggat taaagtaagg caattatgta aactccttag aggaaccaaa gcactaacag    3420
aagtaatacc actaacagaa gaagcagagc tagaactggc agaaaacaga gagattctaa    3480
aagaaccagt acatggagtg tattatgacc catcaaaaga cttaatagca gaaatacaga    3540
agcaggggca aggccaatgg acatatcaaa tttatcaaga gccatttaaa aatctgaaaa    3600
caggaaaata tgcaagaatg aggggtgccc acactaatga tgtaaaacaa ttaacagagg    3660
cagtgcaaaa aataaccaca gaaagcatag taatatgggg aaagactcct aaatttaaac    3720
tgcccataca aaaggaaaca tgggaaacat ggtggacaga gtattggcaa gccacctgga    3780
ttcctgagtg ggagtttgtt aatacccctc ccttagtgaa attatggtac cagttagaga    3840
aagaacccat agtaggagca gaaaccttct atgtagatgg ggcagctaac agggagacta    3900
aattaggaaa agcaggatat gttactaata gaggaagaca aaaagttgtc accctaactg    3960
acacaacaaa tcagaagact gagttacaag caatttatct agctttgcag gattcgggat    4020
tagaagtaaa catagtaaca gactcacaat atgcattagg aatcattcaa gcacaaccag    4080
```

```
atcaaagtga atcagagtta gtcaatcaaa taatagagca gttaataaaa aaggaaaagg    4140
tctatctggc atgggtacca gcacacaaag gaattggagg aaatgaacaa gtagataaat    4200
tagtcagtgc tggaatcagg aaagtactat ttttagatgg aatagataag gcccaagatg    4260
aacatgagaa atatcacagt aattggagag caatggctag tgattttaac ctgccacctg    4320
tagtagcaaa agaaatagta gccagctgtg ataaatgtca gctaaaagga gaagccatgc    4380
atggacaagt agactgtagt ccaggaatat ggcaactaga ttgtacacat ttagaaggaa    4440
aagttatcct ggtagcagtt catgtagcca gtggatatat agaagcagaa gttattccag    4500
cagaaacagg gcaggaaaca gcatattttc ttttaaaatt agcaggaaga tggccagtaa    4560
aaacaataca tactgacaat ggcagcaatt tcaccggtgc tacggttagg gccgcctgtt    4620
ggtgggcggg aatcaagcag gaatttggaa ttccctacaa tccccaaagt caaggagtag    4680
tagaatctat gaataaagaa ttaaagaaaa ttataggaca ggtaagagat caggctgaac    4740
atcttaagac agcagtacaa atggcagtat tcatccacaa ttttaaaaga aaaggggga    4800 ttggggggta cagtgcaggg gaaagaatag tagacataat agcaacagac atacaaacta    4860
aagaattaca aaaacaaatt acaaaaattc aaaattttcg ggtttattac agggacagca    4920
gaaatccact ttggaaagga ccagcaaagc tcctctggaa aggtgaaggg gcagtagtaa    4980
tacaagataa tagtgacata aaagtagtgc caagaagaaa agcaaagatc attagggatt    5040
atggaaaaca gatggcaggt gatgattgtg tggcaagtag acaggatgag gattagaaca    5100
tggaaaagtt tagtaaaaca ccatatgtat gtttcaggga aagctagggg atggttttat    5160
agacatcact atgaaagccc tcatccaaga ataagttcag aagtacacat cccactaggg    5220
gatgctagat tggtaataac aacatattgg ggtctgcata caggagaaag agactggcat    5280
ttgggtcagg gagtctccat agaatggagg aaaaagagat atagcacaca agtagaccct    5340
gaactagcag accaactaat tcatctgtat tactttgact gtttttcaga ctctgctata    5400
agaaaggcct tattaggaca catagttagc cctaggtgtg aatatcaagc aggacataac    5460
aaggtaggat ctctacaata cttggcacta gcagcattaa taacaccaaa aaagataaag    5520
ccacctttgc ctagtgttac gaaactgaca gaggatagat ggaacaagcc ccagaagacc    5580
aagggccaca gagggagcca cacaatgaat ggacactaga gcttttagag gagcttaaga    5640
atgaagctgt tagacatttt cctaggattt ggctccatgg cttagggcaa catatctatg    5700
aaacttatgg ggatacttgg gcaggagtgg aagccataat aagaattctg caacaactgc    5760
tgtttatcca ttttcagaat tgggtgtcga catagcagaa taggcgttac tcgacagagg    5820
agagcaagaa atggagccag tagatcctag actagagccc tggaagcatc caggaagtca    5880
gcctaaaact gcttgtacca attgctattg taaaaagtgt tgctttcatt gccaagtttg    5940
tttcataaca aaagccttag gcatctccta tggcaggaag aagcggagac agcgacgaag    6000
agctcatcag aacagtcaga ctcatcaagc ttctctatca aagcagtaag tagtacatgt    6060
aacgcaacct ataccaatag tagcaatagt agcattagta gtagcaataa taatagcaat    6120
agttgtgtgg tccatagtaa tcatagaata taggaaaata ttaagacaaa gaaaaataga    6180
caggttaatt gatagactaa tagaaagagc agaagacagt ggcaatgaga gtgaaggaga    6240
aatatcagca cttgtggaga tggggtggaa gatggggcac catgctcctt gggatgttga    6300
tgatctgtag tgctacagaa aaattgtggg tcacagtcta ttatgggta cctgtgtgga    6360 aggaagcaac caccactcta ttttgtgcat cagatgctaa agcatatgat acagaggtac    6420
ataatgtttg ggccacacat gcctgtgtac ccacagaccc caacccacaa gaagtagtat    6480
```

```
tggtaaatgt gacagaaaat tttaacatgt ggaaaaatga catggtagaa cagatgcatg    6540
aggatataat cagtttatgg gatcaaagcc taaagccatg tgtaaaatta accccactct    6600
gtgttagttt aaagtgcact gatttgaaga atgatactaa taccaatagt agtagcggga    6660
gaatgataat ggagaaagga gagataaaaa actgctcttt caatatcagc acaagcataa    6720
gaggtaaggt gcagaaagaa tatgcatttt tttataaact tgatataata ccaatagata    6780
atgatactac cagctataag ttgacaagtt gtaacacctc agtcattaca caggcctgtc    6840
caaaggtatc ctttgagcca attcccatac attattgtgc cccggctggt tttgcgattc    6900
taaaatgtaa taataagacg ttcaatggaa caggaccatg tacaaatgtc agcacagtac    6960
aatgtacaca tggaattagg ccagtagtat caactcaact gctgttaaat ggcagtctag    7020
cagaagaaga ggtagtaatt agatctgtca atttcacgga caatgctaaa accataatag    7080
tacagctgaa cacatctgta gaaattaatt gtacaagacc caacaacaat acaagaaaaa    7140
gaatccgtat ccagagagga ccagggagag catttgttac aataggaaaa ataggaaata    7200
tgagacaagc acattgtaac attagtagag caaaatggaa taacacttta aaacagatag    7260
ctagcaaatt aagagaacaa tttggaaata taaaacaat aatctttaag caatcctcag    7320
gaggggaccc agaaattgta acgcacagtt ttaattgtgg aggggaattt ttctactgta    7380
attcaacaca actgtttaat agtacttggt ttaatagtac ttggagtact gaagggtcaa    7440
ataacactga aggaagtgac acaatcaccc tcccatgcag aataaaacaa attataaaca    7500
tgtggcagaa agtaggaaaa gcaatgtatg cccctcccat cagtggacaa attagatgtt    7560
catcaaatat tacagggctg ctattaacaa gagatggtgg taatagcaac aatgagtccg    7620
agatcttcag acctggagga ggagatatga gggacaattg gagaagtgaa ttatataaat    7680
ataaagtagt aaaaattgaa ccattaggag tagcacccac caaggcaaag agaagagtgg    7740
tgcagagaga aaaaagagca gtgggaatag gagctttgtt ccttgggttc ttgggagcag    7800
caggaagcac tatgggcgca gcctcaatga cgctgacggt acaggccaga caattattgt    7860
ctggtatagt gcagcagcag aacaatttgc tgagggctat tgaggcgcaa cagcatctgt    7920
tgcaactcac agtctggggc atcaagcagc tccaggcaag aatcctggct gtggaaagat    7980
acctaaagga tcaacagctc ctggggattt ggggttgctc tggaaaactc atttgcacca    8040
ctgctgtgcc ttggaatgct agttggagta ataaatctct ggaacagatt tggaatcaca    8100
cgacctggat ggagtgggac agagaaatta acaattacac aagcttaata cactccttaa    8160
ttgaagaatc gcaaaccag caagaaaaga atgaacaaga attattggaa ttagataaat    8220
gggcaagttt gtggaattgg tttaacataa caaattggct gtggtatata aaattattca    8280
taatgatagt aggaggcttg gtaggtttaa gaatagtttt tgctgtactt tctatagtga    8340
atagagttag gcagggatat tcaccattat cgtttcagac ccacctccca accccgaggg    8400
gacccgacag gcccgaagga atagaagaag aaggtggaga gagagacaga gacagatcca    8460
ttcgattagt gaacggatcc ttggcactta tctgggacga tctgcggagc ctgtgcctct    8520
tcagctacca ccgcttgaga gacttactct tgattgtaac gaggattgtg gaacttctgg    8580
gacgcagggg gtgggaagcc ctcaaatatt ggtggaatct cctacagtat tggagtcagg    8640
aactaaagaa tagtgctgtt agcttgctca atgccacagc catagcagta gctgagggga    8700 cagataggt tatagaagta gtacaaggag cttgtagagc tattcgccac ataccagaa     8760 gaataagaca gggcttggaa aggatttgc tataagatgg gtggcaagtg gtcaaaagt     8820 agtgtgattg gatggcctac tgtaagggaa agaatgagac gagctgagcc agcagcagat    8880
```

-continued

```
agggtgggag cagcatctcg agacctggaa aaacatggag caatcacaag tagcaataca    8940
gcagctacca atgctgcttg tgcctggcta gaagcacaag aggaggagga ggtgggtttt    9000
ccagtcacac ctcaggtacc tttaagacca atgacttaca aggcagctgt agatcttagc    9060
cactttttaa aagaaaaggg gggactgaaa gggctaattc actcccaaag aagacaagat    9120
atccttgatc tgtggatcta ccacacacaa ggctacttcc ctgattagca gaactacaca    9180
ccagggccag gggtcagata tccactgacc tttggatggt gctacaagct agtaccagtt    9240
gagccagata agatagaaga ggccaataaa ggagagaaca ccagcttgtt cacccctgtg    9300
agcctgcatg ggatggatga cccggagaga gaagtgttag agtggaggtt tgacagccgc    9360
ctagcatttc atcacgtggc ccgagagctg catccggagt acttcaagaa ctgctgacat    9420
cgagcttgct acaagggact ttccgctggg gactttccag ggaggcgtgg cctgggcggg    9480
actggggagt ggcgagccct cagatcctgc atataagcag ctgcttttg cctgtactgg    9540 gtctctctgg ttagaccaga tctgagcctg ggagctctct ggctaactag ggaacccact    9600
gcttaagcct caataaagct tgccttgagt gcttcaagta gtgtgtgccc gtctgttgtg    9660
tgactctggt aactagagat ccctcagacc cttttagtca gtgtggaaaa tctctagca    9719
```

```
<210> SEQ ID NO 2
<211> LENGTH: 1334
<212> TYPE: DNA
<213> ORGANISM: Streptococcus anginosus
<220> FEATURE:
<221> NAME/KEY: UNSURE
<222> LOCATION: (412)
<223> OTHER INFORMATION: n at position 412 is uncertain
<220> FEATURE:
<221> NAME/KEY: UNSURE
<222> LOCATION: (449)
<223> OTHER INFORMATION: n at position 449 is uncertain
<220> FEATURE:
<221> NAME/KEY: UNSURE
<222> LOCATION: (701)
<223> OTHER INFORMATION: n at position 701 is uncertain
<220> FEATURE:
<221> NAME/KEY: UNSURE
<222> LOCATION: (855)
<223> OTHER INFORMATION: n at position 855 is uncertain
<220> FEATURE:
<221> NAME/KEY: UNSURE
<222> LOCATION: (869)
<223> OTHER INFORMATION: n at position 869 is uncertain
<220> FEATURE:
<221> NAME/KEY: UNSURE
<222> LOCATION: (909)
<223> OTHER INFORMATION: n at position 909 is uncertain
<220> FEATURE:
<221> NAME/KEY: UNSURE
<222> LOCATION: (1018)
<223> OTHER INFORMATION: n at position 1018 is uncertain
<220> FEATURE:
<221> NAME/KEY: UNSURE
<222> LOCATION: (1070)
<223> OTHER INFORMATION: n at position 1070 is uncertain
<220> FEATURE:
<221> NAME/KEY: UNSURE
<222> LOCATION: (1121)
<223> OTHER INFORMATION: n at position 1121 is uncertain
<220> FEATURE:
<221> NAME/KEY: UNSURE
<222> LOCATION: (1228)
<223> OTHER INFORMATION: n at position 1228 is uncertain
<220> FEATURE:
<221> NAME/KEY: UNSURE
<222> LOCATION: (1304)
<223> OTHER INFORMATION: n at position 1304 is uncertain

<400> SEQUENCE: 2
```

-continued

```
gaacgggtga gtaacgcgta ggtaacctgc ctattagagg gggataacta ttggaaacga        60
tagctaatac cgcataacag tatgtaacac atgttagatg cttgaaagat gcaattgcat       120
cgctagtaga tggacctgcg ttgtattagc tagtaggtag ggtaaaggcc tacctaggca       180
acgatacata gccgacctga gagggtgatc ggccacactg ggactgagac acggcccaga       240
ctcctacggg aggcagcagt agggaatctt cggcaatggg gggaaccctg accgagcaac       300
gccgcgtgag tgaagaaggt tttcggatcg taaagctctg ttgttaagga agaacgagtg       360
tgagaatgga aagttcatac tgtgacggta cttaaccaga aagggacggc tnactacgtg       420
ccagcagccg cggtaatacg taggtcccna gcgttgtccg gatttattgg gcgtaaagcg       480
agcgcaggcg gttagaaaag tctgaagtga aaggcagtgg ctcaaccatt gtaggctttg       540
gaaactgttt aacttgagtg cagaaggggga gagtggaatt ccatgtgtag cggtgaaatg       600
cgtagatata tggaggaaca ccggtggcga aagcggctct ctggtctgta actgacgctg       660
aggctcgaaa gcgtggggag cgaacaggat tagataccct ngtagtccac gccgtaaacg       720
atgagtgcta ggtgttgggt cctttccggg actcagtgcc gcagctaacg cattaagcac       780
tccgcctggg gagtacgacc gcaaggttga aactcaaagg aattgacggg ggccgcacaa       840
gcggtggagc atgtngttta attcgaagna acgcgaagaa ccttaccagg tcttgacatc       900
ccgatgctnt ttctagagat aggaagtttc ttcggaacat cggtgacagg tggtgcatgg       960
ttgtcgtcag ctcgtgtcgt gagatgttgg gttaagtccc gcaacgagcg caaccctnat      1020
tgttagttgc catcattaag ttgggcactc tagcgagact gccggtaatn aaccggagga      1080
aggtggggat gacgtcaaat catcatgccc cttatgacct nggctacaca cgtgctacaa      1140
tggctggtac aacgagtcgc aagccggtga cggcaagcta atctctgaaa gccagtctca      1200
gttcggattg taggctgcaa ctcgcctnca tgaagtcgga atcgctagta atcgcggatc      1260
agcacgccgc ggtgaatacg ttcccgggcc ttgtacacac cgcncgtcac accacgagag      1320
tttgtaacac ccga                                                       1334
```